United States Patent
Krueger

(10) Patent No.: US 9,298,985 B2
(45) Date of Patent: Mar. 29, 2016

(54) PHYSIOLOGICAL BIOSENSOR SYSTEM AND METHOD FOR CONTROLLING A VEHICLE OR POWERED EQUIPMENT

(71) Applicant: Wesley W. O. Krueger, San Antonio, TX (US)

(72) Inventor: Wesley W. O. Krueger, San Antonio, TX (US)

( * ) Notice: Subject to any disclaimer, the term of this patent is extended or adjusted under 35 U.S.C. 154(b) by 79 days.

(21) Appl. No.: 14/172,734

(22) Filed: Feb. 4, 2014

(65) Prior Publication Data

US 2014/0152792 A1 Jun. 5, 2014

Related U.S. Application Data

(63) Continuation-in-part of application No. 13/108,683, filed on May 16, 2011, now Pat. No. 8,690,750.

(51) Int. Cl.
| | |
|---|---|
| *G01C 23/00* | (2006.01) |
| *G06K 9/00* | (2006.01) |
| *A61M 21/00* | (2006.01) |
| *G02B 27/01* | (2006.01) |

(52) U.S. Cl.
CPC ........... *G06K 9/00604* (2013.01); *A61M 21/00* (2013.01); *G01C 23/00* (2013.01); *G02B 27/017* (2013.01); *A61M 2021/0022* (2013.01); *A61M 2021/0027* (2013.01); *A61M 2021/0044* (2013.01); *A61M 2021/0083* (2013.01); *A61M 2205/18* (2013.01); *A61M 2205/3569* (2013.01); *A61M 2205/3592* (2013.01); *A61M 2205/507* (2013.01); *A61M 2210/0612* (2013.01); *A61M 2230/04* (2013.01); *A61M 2230/10* (2013.01); *A61M 2230/201* (2013.01); *A61M 2230/205* (2013.01); *A61M 2230/207* (2013.01); *A61M 2230/208* (2013.01); *A61M 2230/30* (2013.01); *A61M 2230/40* (2013.01); *A61M 2230/50* (2013.01); *A61M 2230/60* (2013.01); *A61M 2230/62* (2013.01); *A61M 2230/63* (2013.01); *G02B 2027/0138* (2013.01); *G02B 2027/0187* (2013.01)

(58) Field of Classification Search
CPC ................ A61M 21/02; A61M 21/00; A61M 2021/004; A61M 2021/005; G06K 9/00604; G01C 23/00; G02B 27/017; A61B 3/00; A61B 3/0041; A61B 3/0058; A61B 3/0091; A61B 3/10; A61B 3/113; A61B 3/14; A61B 3/145
USPC ......................................... 600/26–28; 348/78
See application file for complete search history.

(56) References Cited

U.S. PATENT DOCUMENTS

| | | |
|---|---|---|
| 3,157,852 A | 11/1964 | Hirsch |
| 4,028,725 A | 6/1977 | Lewis |
| 4,326,189 A | 4/1982 | Crane |

(Continued)

*Primary Examiner* — Jacqueline Cheng
*Assistant Examiner* — Thaddeus Cox
(74) *Attorney, Agent, or Firm* — Kilpatrick Townsend & Stockton LLP

(57) ABSTRACT

A head-mounted video-camera-based eye sensor system and method for measuring palpebral movement is disclosed. The system and method comprise a display that includes at least one display element responsive to palpebral movement information from the eye sensor. The system and method also comprise an electronic interface to a vehicle or powered equipment to transmit the palpebral movement information to the vehicle or powered equipment. The system and method can be used to alert the user, the vehicle, and/or the powered equipment to the fact that a person might be experiencing vertigo, motion sickness, motion intolerance, and/or spatial disorientation.

20 Claims, 12 Drawing Sheets

(56) References Cited

U.S. PATENT DOCUMENTS

| | | | |
|---|---|---|---|
| 5,051,735 A | 9/1991 | Furukawa | |
| 5,067,941 A | 11/1991 | Hendricks | |
| 5,486,821 A | 1/1996 | Stevens et al. | |
| 5,555,895 A * | 9/1996 | Ulmer | A61B 3/113 351/210 |
| 5,583,795 A * | 12/1996 | Smyth | 702/150 |
| 5,599,274 A | 2/1997 | Widjaja et al. | |
| 5,629,848 A | 5/1997 | Repperger et al. | |
| 5,635,947 A | 6/1997 | Iwamoto | |
| 5,790,085 A | 8/1998 | Hergesheimer | |
| 5,966,680 A * | 10/1999 | Butnaru | 702/150 |
| 6,228,021 B1 | 5/2001 | Kania | |
| 6,361,508 B1 | 3/2002 | Johnson et al. | |
| 6,364,845 B1 | 4/2002 | Duffy et al. | |
| 6,443,913 B1 | 9/2002 | Kania | |
| 6,497,649 B2 | 12/2002 | Parker | |
| 6,568,396 B1 | 5/2003 | Anthony | |
| 6,896,655 B2 | 5/2005 | Patton et al. | |
| 6,924,428 B1 | 8/2005 | Payne et al. | |
| 6,932,090 B1 * | 8/2005 | Reschke et al. | 128/898 |
| 7,128,705 B2 | 10/2006 | Brendley et al. | |
| 7,183,946 B2 | 2/2007 | Boudrieau | |
| 7,266,446 B1 | 9/2007 | Pelosi | |
| 7,331,671 B2 * | 2/2008 | Hammoud | 351/210 |
| 7,401,920 B1 * | 7/2008 | Kranz | A61B 3/113 351/209 |
| 7,474,335 B2 | 1/2009 | Basson et al. | |
| 7,490,611 B2 | 2/2009 | Bromwich | |
| 7,646,394 B1 | 1/2010 | Neely et al. | |
| 7,667,700 B1 | 2/2010 | Neely et al. | |
| 7,717,841 B2 | 5/2010 | Brendley et al. | |
| 7,722,526 B2 | 5/2010 | Kim | |
| 7,893,935 B1 | 2/2011 | Neely et al. | |
| 7,925,391 B2 | 4/2011 | Sanders-Reed | |
| 8,063,798 B2 | 11/2011 | Cernasov et al. | |
| 8,218,006 B2 | 7/2012 | De Mers et al. | |
| 8,690,750 B2 | 4/2014 | Krueger | |
| 2001/0028309 A1 * | 10/2001 | Torch | 340/575 |
| 2004/0097839 A1 * | 5/2004 | Epley | A61B 5/0484 600/595 |
| 2005/0099601 A1 * | 5/2005 | MacDougall | A61B 3/113 351/209 |
| 2006/0253001 A1 | 11/2006 | Small et al. | |
| 2009/0312817 A1 | 12/2009 | Hogle et al. | |
| 2009/0326604 A1 | 12/2009 | Tyler et al. | |
| 2010/0141555 A1 * | 6/2010 | Rorberg | G02B 27/017 345/8 |
| 2010/0198104 A1 * | 8/2010 | Schubert | A61B 3/113 600/558 |
| 2011/0028872 A1 | 2/2011 | Kevin | |
| 2011/0029045 A1 | 2/2011 | Cevette et al. | |
| 2011/0045446 A1 | 2/2011 | Glaser et al. | |
| 2011/0176106 A1 * | 7/2011 | Lewkowski | A61B 3/112 351/206 |

\* cited by examiner

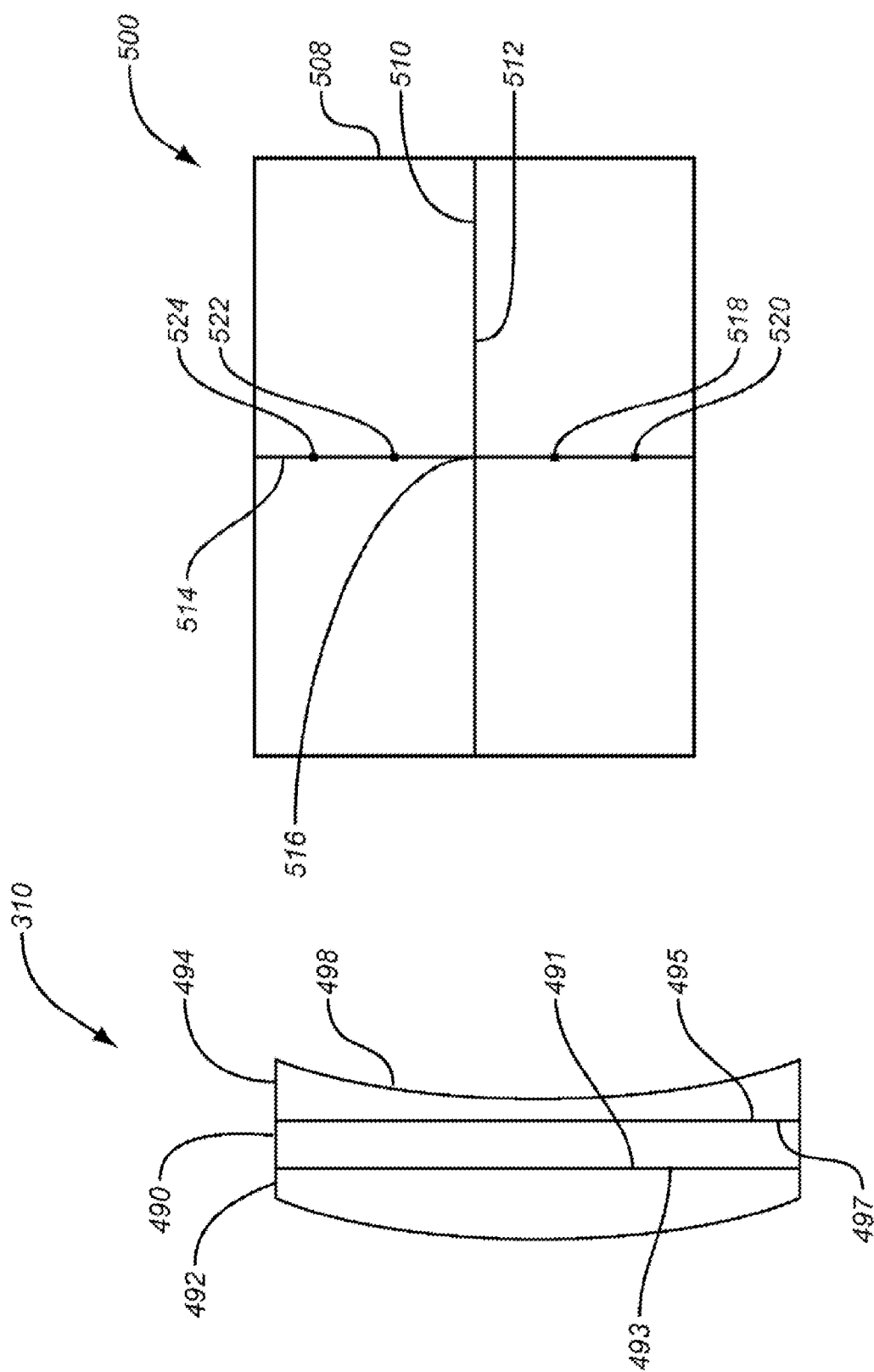

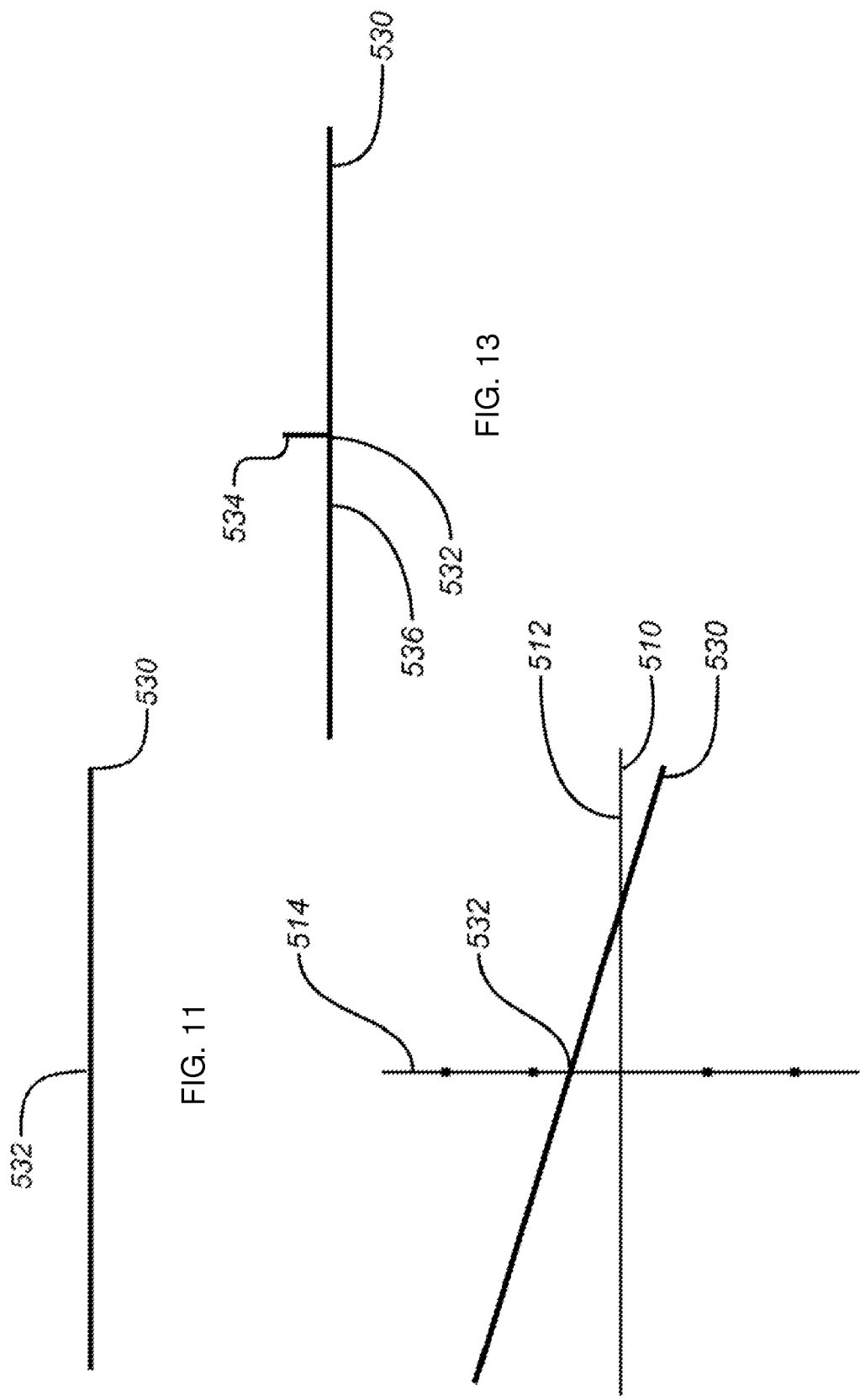

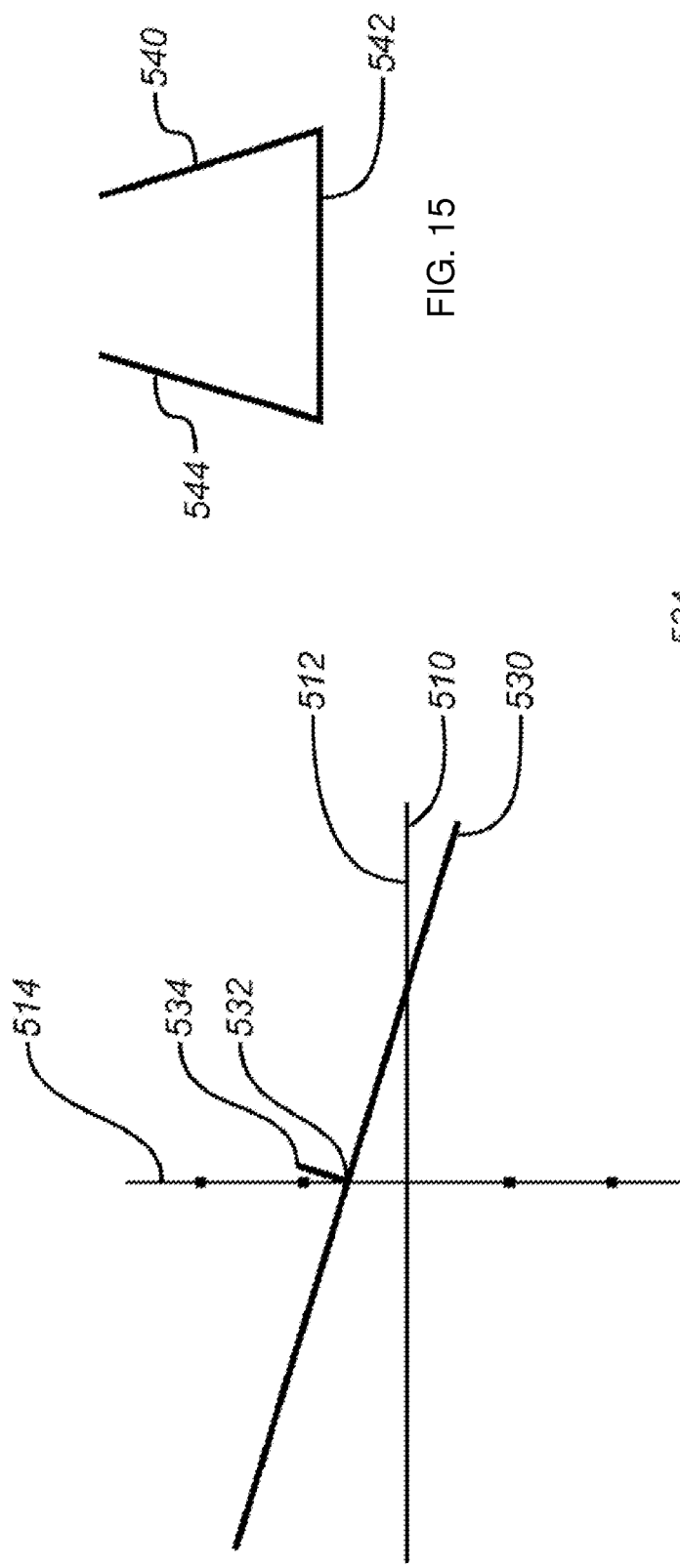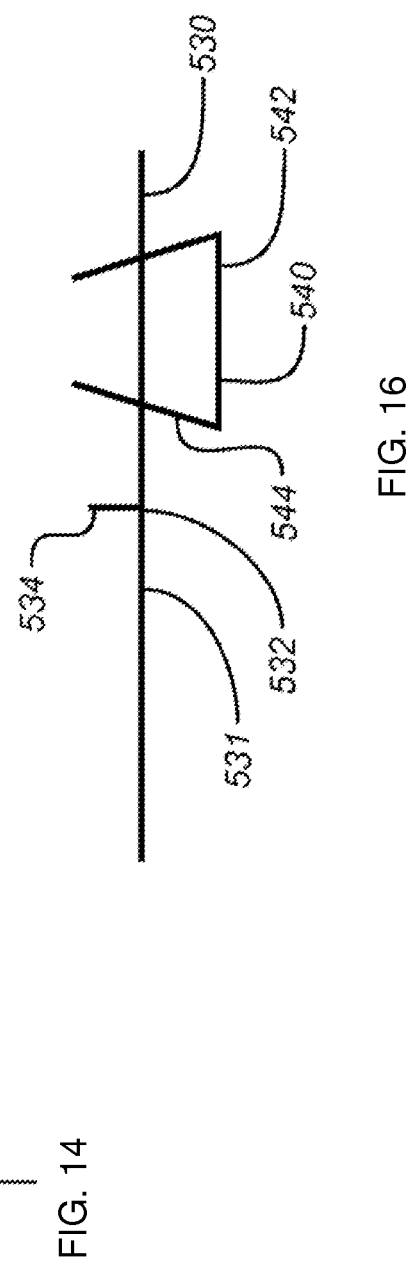

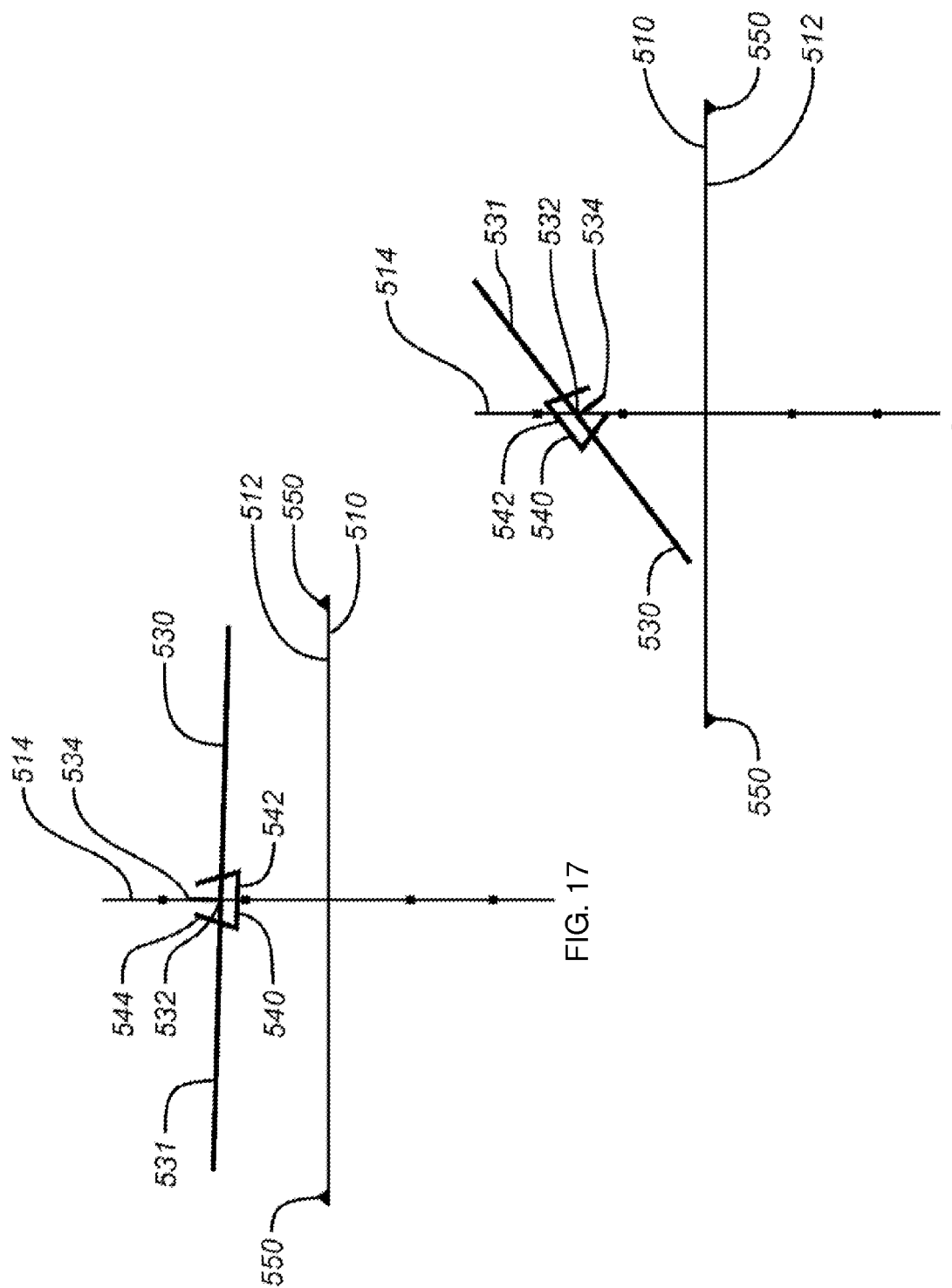

PHYSIOLOGICAL BIOSENSOR SYSTEM AND METHOD FOR CONTROLLING A VEHICLE OR POWERED EQUIPMENT

CROSS-REFERENCE TO RELATED APPLICATIONS

This application is a continuation-in-part of U.S. application Ser. No. 13/108,683 filed May 16, 2011, which is hereby incorporated by reference in its entirety.

BACKGROUND

The present invention generally relates to systems and methods for avoiding problems associated with vertigo, motion sickness and spatial disorientation that compromise human performance or lead to loss of control of a vehicle or powered equipment. The method used can specifically monitor the physiological effect of vertigo, motion sickness, motion intolerance, or spatial disorientation.

Motion sickness, spatial disorientation and vertigo have been acknowledged as a widespread problem, affecting a significant portion of world population to varying degrees. Researchers report that up to 60% of the population has some motion intolerance. It has been reported that motion sickness affects nearly one third of all people who travel by land, sea, or air. Individuals are affected daily by motion sickness and spatial disorientation while riding in automobiles, trains, buses, planes or other transport. The Greeks provided the first written historical account of motion sickness. The Roman Cicero claimed he would rather be killed in battle than suffer the tortures of nausea maris. Motion sickness has even been used as a form of punishment. One of the world's most famous mariners, Admiral Lord Nelson reportedly never adapted to motion sickness. Napoleon's General Carbuccia refused to use camels for Napoleon's army, because of the issues with motion (2) Even Lawrence of Arabia is reported to have experienced Camel sickness.

It is also known that some people are more susceptible than others; for example, women are more sensitive to motion than men by a ratio of about 5:3. Some are more susceptible due to physical reasons such as age. Studies show a significant genetic contribution to a propensity to motion sickness. It has been well observed that poor ventilation, bad odors, smoking, eating large fatty meals and high blood alcohol levels can make motion sickness more pronounced. Susceptibility to motion sickness begins at about age two, and for most will peak in adolescence and decline gradually. However, many adults remain highly sensitive caused by any motion, particularly when combined with either an absence of a visual reference or to significant levels of visual stimuli. In fact, a provocative visual stimulus has been shown to be the most influential cause of motion sickness symptoms. Reading in a moving vehicle, abruptly moving the head (such as looking down) while a vehicle is moving can provoke symptoms. Fear, anxiety and other psychological factors can contribute to the onset of motion sickness. Some people can get sick just thinking about an upcoming trip or flight.

For those who experience the symptoms, the result is often disabling, with nausea, vomiting, sweating, and unsteadiness, while feeling cold, clammy and disorientated. In addition, the term "sopite syndrome" was coined to refer to the apathy, passivity, and lack of concentration characteristic of motion sickness.

The occurrence of motion sickness can approach 100% in cruise ship passengers on rough seas. Seasickness, a common form of motion sickness, is frequent among naval personnel, where 60% to 90% percent of inexperienced sailors can suffer from seasickness. Experienced crewmembers are not immune—up to 60% of experienced crewmembers have been affected in these conditions. This becomes a major problem in modern seamanship in which small crews are responsible for the operation of sensitive and sophisticated equipment. During the invasion of Normandy, in World War II, the seas were reportedly very high causing the landing crafts to pitch and yaw, like a kite in a windstorm. The soldiers were lying and sitting in flat bottomed crafts and were using huge buckets for vomiting and urinating, which soon overflowed after boarding. As thousands of men were lying in the vomit, urine and rain they debarked in a state of terror, which was compounded by their symptoms of seasickness, and attempted to perform at a high level in order to survive in combat. Many of these soldiers had to overcome the most debilitating effects of motion sickness to survive. Volumes of data document the severe effect of motion sickness on human performance of even basic tasks.

Spatial disorientation along with motion sickness are significant problems in aviation. In motion provocative environments, spatial disorientation and motion sickness cause not only a loss in human performance (affecting cognitive and motor skills), but a loss of expensive aircraft and human life. Thousands of deaths have been attributed to aviation accidents caused by being spatially disoriented. A recent study has shown that almost Ninety to One Hundred percent (90-100%) of aircrew have reported at least one incidence of spatial disorientation (SD) during their flying careers. SD accounted for Eleven to Fourteen percent (11-14%) of USAF mishaps and a mishap fatality rate of 69%, with risk of SD significantly increased in helicopters and fighter/attack aircraft and at night. The most frequent experienced SD episodes are "leans" (Ninety-Two percent (92%)), loss of horizon due to atmospheric conditions (Eighty-Two percent (82%)), misleading altitude cues (Seventy-Nine percent 79%)), sloping horizon (Seventy-Five percent (75%)), and SD arising from distraction (Sixty-Six percent (66%)). A review of aviation mishaps from 1987-1997 showed that there was an average of one fatal SD accident every Eleven (11) days in the United States. The death of John F. Kennedy Jr. was an example of a spatial disorientation accident and unknown to many were thirty other reported crashes that same day, with at least one other due to spatial disorientation. According to FAA statistics, SD and loss of situational awareness causes Fifteen to Seventeen percent (15%-17%) of fatal general aviation crashes annually. More significantly, Nine (9) out of ten (10) SD mishaps result in a fatality. The Air Force Safety Center FY93-02 mishap analysis reported that Class A mishaps resulted in Two Hundred Forty-Three (243) destroyed aircraft, Three Hundred Ten (310) fatalities, and an economic loss of Six Billion Two Hundred Thirty Million dollars ($6.23 billion). Airsickness has also been identified as a flight training issue. A motion sickness history questionnaire obtained from student pilots in the Air Force revealed an incidence of airsickness of fifty percent (50%). In a questionnaire to B-1 and B-52 bomber crewmembers, it was reported to be a frequent occurrence among non-pilots in both aircraft, and experienced crewmembers were more likely to report an impact on their duties.

Space motion sickness is experienced by Sixty to Eighty percent (60%-80%) of astronauts during the first Two to Three (2-3) days in micro gravity and by a similar proportion during their first few days after return to Earth. Up to Ninety percent (90%) of astronauts experience spatial disorientation during reentry and landing of the shuttle, with prevalence proportional to the length of the mission. Exposure to micro gravity rearranges the relationships among signals from visual, skin, joint, muscle, and vestibular receptors. Congruence between vestibular signals and those from other receptors, as well as between the vestibular otolith and semicircular canal receptors, is disrupted by the absence of gravity. This lack of congruence between sensory exposure to provocative real or apparent motion leads to the progressive cardinal symptoms of terrestrial motion sickness. Space motion sickness may vary slightly with flushing more common than pallor, stomach awareness, malaise, loss of appetite, and sudden vomiting, often without prodromal nausea.

Simulator sickness is another example of motion sickness, and many military pilots have reported at least one symptom following simulator exposure. In a study of Coast Guard aviators undergoing flight simulator testing, Sixty-Four percent (64%) reported adverse symptoms during the first simulator flight and Thirty-Nine percent (39%) did so during the last flight. Thirty-Six percent (36%) of pilots reported motion sickness when training on a Blackhawk flight simulator.

More recently, simulator sickness in virtual environments (VE) has become an important issue. Virtual reality is already a popular technology for entertainment purposes, and both the U.S. Army and Navy are interested in the training applications of virtual environments. However, some users of VE experience discomfort during, and sometimes after, a session in a simulated environment, in equivalent fashion to simulator sickness already noted for flight and driving simulators.

There have been many theories about the cause of motion sickness, spatial disorientation and vertigo. The earlier Gut Theory proposed that vomiting was a reflex response to irritation of the gastric mucosa possibly caused by movements of the viscera which caused abdominal contractions and overstimulated the Pacinian corpuscles or overproduction of bile in the liver. There are also Vascular or Blood Theories: those that proposed a lack of blood flow to the brain (cerebral anemia) and those that proposed too much blood going to the brain (cerebral hyperemia). These conditions were theorized to be caused by numerous mechanisms. One such theory suggested that vascular deficiency was due to the irritation of the eyes by perceived motion, which, by reflex action, produced spasm in the cerebral capillaries causing giddiness and vomiting. Other vascular theories argued that motion produced cerebral hyperemia, which destabilized brain cells in the vomiting center of the medulla oblongata.

Other theories attributed it to respiratory factors, shock to the central and autonomic nervous system, or due to infections. The vestibular and other sensory contributions came later, and were built upon some of the early work of Purkinje, Flourens, and Meniere.

Over-stimulation of the semicircular canals theory evolved in the 1990s. This lost favor when it became clear that motion in the absence of vestibular stimulation could be as provocative as the primary sensory organs.

A fluid shift theory with assumptions of active or passive shifts in the body fluids to the central nervous system and vestibulo-auditory mechanisms was considered a cause in space flight.

The neural mismatch theory suggested the problems to be in the central integrative mechanism, which is involved in interpreting the significance of the sensory environment. It was proposed that the conflict between visual or vestibular input systems or between separate components of the vestibular system is of secondary importance to mismatch occurring between ongoing sensory experience and long-term memory. The limbic system was suspected as perhaps being the neural mismatch center of the brain.

Currently, the sensory conflict theory appears to be the dominant theory favored by researchers in that the majority of investigators agree that it is not solely the movement or movement stimulus that results in motion sickness, but rather a conflict in movement information detected by the different sensory modalities of the inner ear, vision, and proprioception. A conflict of visual and vestibular (inner ear) information, as it relates to postural control and visual stabilization, is certainly a critical factor. Investigators now also agree that it is primarily an incongruence of visual and vestibular sensory information regarding movement and orientation that results in motion sickness. Incongruence between the semicircular canals and the otolithic organ input has also been implicated as the provocative stimulus in seasickness and in the onset of motion sickness associated with weightlessness. Another contributing factor which may trigger susceptibility to motion sickness may be the mass size differences of the utricular otoconia between the left and right sides in some people, as seen in fish.

Within the sensory conflict concept has arisen an 'incongruence in the visual system' theory which can be called a Velocity Storage Theory. The vestibular nerve communicates head velocity and estimates of angular displacements require further central nervous system processing (i.e. integration). There is some inconsistency between velocity-based ocular studies and displacement-based perceptual studies. Most oculographic studies of vestibular function are based on measurements of the slow phase velocity of the eye. If a monkey or man is rotated at constant velocity in the dark, the velocity of the slow phase of the nystagmus decays exponentially with a time constant of Fifteen to Twenty seconds (15-20 sec). Direct recordings of the vestibular nerve in monkeys have shown the head velocity signal, transmitted by the vestibular nerve, has a time constant of decay of only Seven to Ten (7-10 sec). The duration of the eye velocity curve (i.e. a nystagmus response) is therefore longer, outlasting the sensation or perception curve. The perception of angular velocity is based on signals subserved by the brainstem velocity storage system. Thus the head velocity signal appears to be stored in the brain and then released onto ocular motor neurons for the generation of nystagmus. Brainstem circuits in the vicinity of the vestibular nuclei, behaving as mathematical integrators, are thought to mediate this storage process. There is evidence that motion sickness is generated through this velocity storage and can be reduced by reducing the angular vestibular ocular reflex time constant. Others support a multi-factor explanation of motion sickness, involving both sensory conflict and eye movement.

Vestibular Dysfunction. Postural control requires a complex interaction of visual and proprioceptive sensory inputs providing external orientation reference frames while the internal reference frame is provided by the vestibular system. An estimated Twenty percent (20%) of the general population is affected by a vestibular disorder. Ninety million (9 million) Americans (Forty-Two percent (42%) of the population) will complain of dizziness at least once during lifetime, and, of these, Eight percent (80%) will have a vestibular component. There are more than Ten million (10 million) physician visits annually for dizziness or balance complaints (National Balance Centers/Vestibular Disorders Association), with a cost of greater than one billion dollars per year. Persistent vestibular dysfunction can occur following a variety of insults to the vestibular system, including infections, ototoxicity, trauma, chronic ear pathology, tumors, Meniere's disease, surgery and other idiopathic causes. Acoustic tumor surgery and vestibular nerve section, performed for disabling vertigo in patients with Meniere's disease, usually result in rapid compensation. However some patients, particularly non-Meniere's disease patients, have a prolonged period of unsteadiness without compensation for a long period of time. The resulting disability can be devastating. It has also been shown that postural instability precedes motion sickness with provocative visual stimuli. All these vestibular impairments cause disequilibrium, blurred vision, disorientation, and vertigo, which in turn cause dysfunction in many activities of daily living and in social interactions that traditional medical treatments may not address.

Mismatches can be caused where there is a mismatch between stimuli as processed by the brain. Mismatches can occur where there is motion, or where there is no motion. These mismatches may be caused by delays in the delivery or processing of the stimuli or mismatch of stimuli even without delay. Examples of mismatches are seen in persons suffering from vertigo or persons in a virtual space such as a video game or flight simulator or targeting system.

Butnaru in U.S. Pat. No. 5,966,680 taught the use of a device and method which operates as an artificial labyrinth to eliminate sensory mismatch between a person's natural labyrinth vestibular system and the vision system of the user. The device provided the user with an alternative means for determining true orientation within his environment through a system of visual cues. However Butnaru system of cues have been determined to have some limitations and the Butnaru system is lacking in its integration with user environments, which may cause sensory mismatches.

There is a need for improvements to systems which avoid vertigo, motion sickness, and spatial disorientation integrated in motion sensory provocative environments to avoid problems associated with compromised human performance or even loss of user control.

BRIEF DESCRIPTION OF THE DRAWINGS

For a more complete understanding of the present invention and the advantages thereof, reference is now made to the following description taken in conjunction with the accompanying drawings in which like reference numerals indicate like features and wherein:

FIG. 9 illustrates an embodiment of a lens set implementation of the display;

FIG. 10 illustrates and embodiment of a Head Attitude Scale (HAS);

FIG. 11 illustrates an embodiment of a Pitch/Roll Indicator (PRI);

FIG. 12 illustrates an embodiment of a Pitch/Roll Indicator (PRI) of FIG. 11 in conjunction with the HAS of FIG. 10;

FIG. 13 illustrates an alternative embodiment of a Pitch/Roll Indicator (PRI) with a vertical fin;

FIG. 14 illustrates an embodiment of a Pitch/Roll Indicator (PRI) of FIG. 13 in conjunction with the HAS of FIG. 10;

FIG. 15 illustrates an embodiment of a Head-Rotation/Yaw Indicator (Yaw Indicator);

FIG. 16 illustrates an embodiment of the Head-Rotation/Yaw Indicator of FIG. 15 in conjunction with the Pitch Roll Indicator of FIG. 13;

FIG. 17 illustrates an embodiment of the Head-Rotation/Yaw Indicator of FIG. 15 in conjunction with the Pitch Roll Indicator of FIG. 13 in further conjunction with the HAS of FIG. 10; and FIG. 18 illustrates the embodiment of symbology FIG. 17 reflecting different positional circumstances.

Figure 1:
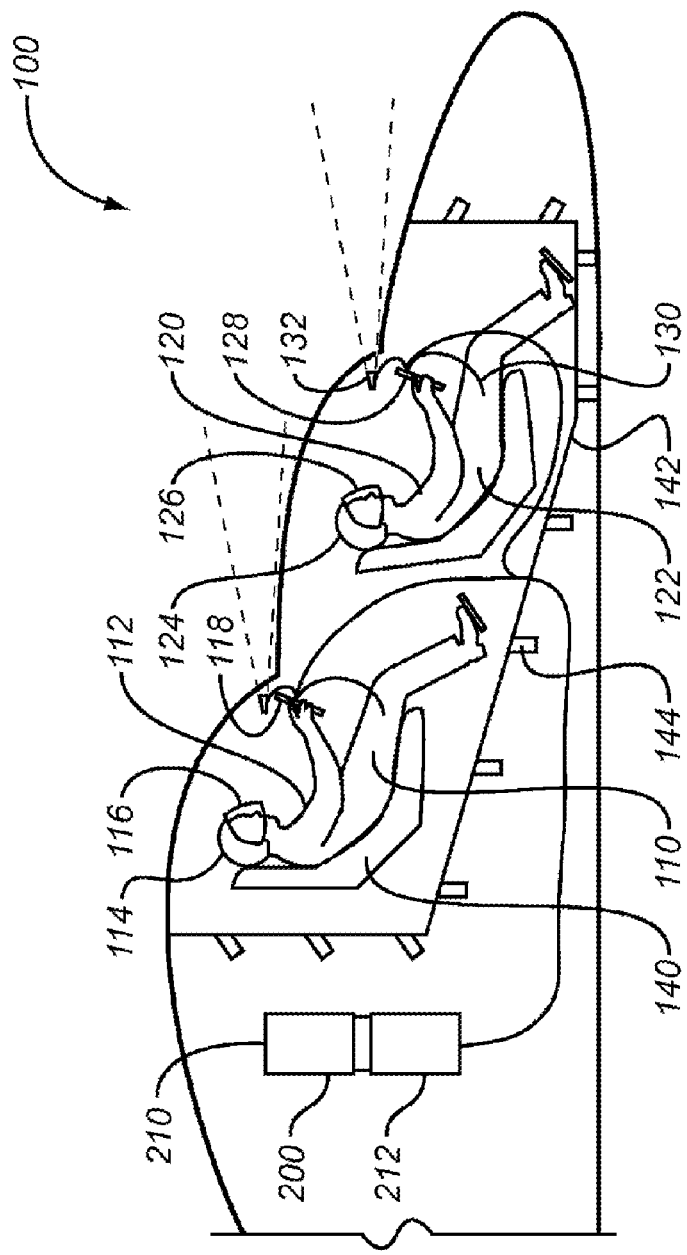
FIG. 1 illustrates an example of an environment that is provocative to motion sickness and spatial disorientation.

It should be understood that the drawings are not necessarily to scale. In certain instances, details that are not necessary for an understanding of the invention or that render other details difficult to perceive may have been omitted. It should be understood that the invention is not necessarily limited to the particular embodiments illustrated herein.

DETAILED DESCRIPTION

The ensuing description provides preferred exemplary embodiment(s) only, and is not intended to limit the scope, applicability or configuration of the disclosure. Rather, the ensuing description of the preferred exemplary embodiment(s) will provide those skilled in the art with an enabling description for implementing a preferred exemplary embodiment. It should be understood that various changes could be made in the function and arrangement of elements without departing from the spirit and scope as set forth in the appended claims. Preferred embodiments of the present invention are illustrated in the Figures, like numerals being used to refer to like and corresponding parts of the various drawings. Specific details are given in the following description to provide a thorough understanding of the embodiments. However, it will be understood by one of ordinary skill in the art that the embodiments may be practiced without these specific details.

1. Definitions.

Basic eye movement systems can be defined by their functional goals, the conditions under which they function, and the presumed distinct neuronal circuitry that forms them. Basic eye movement systems include such descriptions as saccadic, smooth pursuit, and vergence systems, which all act to bring a visual target of interest on the fovea. The fixation, labyrinthine-ocular reflex, and optokinetic systems all help to maintain steady fixation of a target when movement is present. In describing the function and structure of the embodiments in this disclosure, the following definitions shall apply:

A saccade is a fast movement of an eye. Saccades are quick, simultaneous movements of both eyes in the same direction. Humans do not look at a scene in fixed steadiness, the eyes move around, locating interesting parts of the scene and using this information to build up a mental, three-dimensional 'map' corresponding to the scene.

Smooth pursuit eye movements allow the eyes to closely follow a moving object. It is one of two ways that humans can voluntarily shift gaze, the other being saccadic eye movements. Smooth pursuit eye movements are what we use to keep our eyes on and follow a moving object. Smooth pursuit differs from the vestibulo-ocular reflex, which only occurs during movements of the head and serves to stabilize gaze on a stationary object.

The voluntary fixation of the visual system is directly related with the fovea, the central area of the retinas, that provides high-resolution visual stimuli. In human vision, fixation movements have the task to register the target into the foveae, in order to maximize the perceptible details in the area of interest. Studies using orientation sensing elements have documented the importance of fixation particularly in monitoring and controlling the physiological effects of vertigo, motion sickness, motion intolerance, or spatial disorientation. When individuals are sensing vection or perceived rotation, evidence has shown that focusing on the vertex point of an artificial horizon will stop or mitigate the vection or spinning sensation. Similarly, when a person is on a vessel experiencing pitch and roll activity, focusing on an artificial horizon or stable horizontal plane can mitigate or control motion sickness. Vertigo has been more controllable with foveal fixation on a small point and motion sickness is more controllable with visualizing more of an artificial horizon or stable horizontal plane.

Version is defined as the rotation of the eyes about the vertical axis to maintain a constant disparity. Meanwhile, tilt is the rotation of each eye with respect to the horizontal axis. Finally, vergence is the rotation of each eye about the vertical axis to change the disparity.

Vergence is the simultaneous movement of both eyes in opposite directions to obtain or maintain singular binocular vision. The interaction between vision and motor control allows us to develop an active sensor that achieves high accuracy of the disparity computation around the fixation point, and fast reaction time for the vergence control. In this contribution, we address the development of a real-time architecture for vector disparity computation using an FPGA (field programmable gate array) device. We implement the disparity unit and the control module for vergence, version, and tilt to determine the fixation point The optokinetic reflex responds to slip of the image of the visual world on the retina and helps maintain the visual axes on target, as well as providing subjective information about rotation of the head in space at low frequencies of head rotation (<1 Hz). Optokinetic nystagmus (OKN) is the eye movement elicited by the tracking of a moving field. As moving fields contain within them distinct targets, OKN generally contains within it smooth pursuit. Optokinetic function requires that the eyes perform certain motions with the greatest speed and accuracy, which is accomplished by version movements. The optostatic function, which regulates the position of the eyes relative to each other and to the coordinates of space, is subserved by the vergence movements.

Nystagmus is an involuntary rapid movement (horizontal, vertical, rotary, or mixed, i.e., of more than one type) of the eyeball. It is also described as a periodic, rhythmic, involuntary movement of both eyeballs in unison. There is a quick component in one direction and a slow component in the opposite direction. There can be many causes of nystagmus including the inner ear, visual, drugs, or the central nervous system. There are numerous types of nystagmus and various methods of classifying nystagmus. Nystagmus can be divided into two groups. Sensory nystagmus is related to vision loss and motor nystagmus is related to the control of muscle function.

A dongle is a hardware device attached to a computer without which a particular software program will not run. It can be used to prevent unauthorized use. Dongles may also be wireless adapters, which can be device that can be plugged into a USB port to enable wireless access from a computer to an external Wi-Fi device, a mobile phone, or to the internet via high-speed broadband, or to enable wireless connectivity in a printer or other peripheral. A dongle can be used to ensure that only authorized users can use certain software applications. When a program that comes with a dongle runs, it checks the dongle for verification as it is loading. If more than one application requires a dongle, multiple dongles using the same port can be daisy-chained together.

Biometrics refers to technologies or processes that measure and analyze human body characteristics, eye retinas and irises. Biometrics can also include the characteristics of a person's unique physical vital signs and/or blood chemistries and can be recorded by an electronic device. Biometrics can be used for identity authentication. Biometrics can refer to the bioscience of measuring the different aspects of the physiological characteristics or chemical characteristics of the person at a specific time. Authentication by biometric verification is becoming increasingly common in security and in the operation of powered equipment. Biometric devices, such as finger and retinal scanners consist of a sensor or sensing device and software that converts the scanned information into digital form and compares match points as well as a database that stores the biometric data for comparison. In other applications bioscience sensors specifically designed to measure normal or abnormal vital signs or chemical values stored in the database can be used in the safety of operational aspects of vehicles and powered equipment. This biometric analysis also encompasses the bioscience measurement of the movements.

Electroencephalography (EEG) is the recording of electrical activity along the scalp. Electroencephalographic techniques measures voltage fluctuations resulting from ionic current flows within the neurons of the brain. In clinical contexts, EEG refers to the recording of the brain's spontaneous electrical activity over a short period of time, usually 20-40 minutes, as recorded from multiple electrodes placed on the scalp.

Blepharoptosis (e.g. Ptosis) is an abnormal low-lying upper eyelid margin, partially covering the eye, with the eye in primary gaze. Normally, the upper lid covers 1.5 mm of the superior part of the cornea.

Marginal reflex distance is the distance between the center of the pupillary light reflex and the upper eyelid margin with the eye in primary gaze.

2. Purpose and Overview of the Embodiments.

Embodiments of the present invention can utilize a physiologic biosensor system used to control vehicular or other powered equipment which is triggered by the presence of abnormal physiological biometric measurements from eye movements, eyelid activity and/or other electrical or biochemical findings of the operator. One basis for these embodiments is the fact that abnormalities occur with the human operator of equipment or vehicles before any observable activities of the vehicle, which they are operating, or equipment they may be using. Therefore detecting the measured abnormal responses, related to the eye movements, palpebrae (e.g. eyelids), or electrical or biochemical findings have an advantage and unique opportunity to properly control vehicular activity or other equipment activity if human performance has become decayed. The eye tracking and detection of abnormal eye movement, palpebral position or palpebrae position or activity is the input for the controller response. This physiologic biosensor detection is based on measurement of specific abnormal eye movement, eyelid activity (palpebral or palpebrae) measurements, (including such measurements as palpebral closure rate, palpebral closure duration, palpebral fissure height, palpebral aperture, marginal reflex distance, frequency of palpebral closure, and velocity of palpebral closure palpebral position and palpebrae position) or abnormal biometrics detecting vital signs and biochemical parameters. When the abnormal parameters are identified by the sensor, this data is integrated into an algorithm which can then control the vehicular response to a predetermined response, based on the speed, altitude and attitude/orientation. This response may alter the speed, altitude, or attitude of the vehicle or alter the powered equipment to a predetermined "safe" mode and can engage a remote source to assume control. It can provide auditory, haptic, visual, distal, or remote alarms. This response can be faster and can precede any vehicular response, which might have occurred if the abnormal operator response had not been measured. Similarly, when a physiologic biosensor detects specific abnormal electrical or biochemical responses from the operator of a vehicle or powered equipment, an algorithm can be triggered to control the speed, altitude, or attitude of the vehicle or to alter the powered equipment to a predetermined "safe" mode and can engage a remote source to assume control. The algorithm can provide an alarm to the operator either auditorially, haptically, or visually and can provide remote alarms to the user and to the remote source. The abnormal eye movements or eyelid responses (including any palpebral movement which can be measured by the eye sensor and comprised of palpebral position, palpebral closure rate, palpebral closure duration, palpebral fissure height, palpebral aperture, marginal reflex distance, frequency of palpebral closure, and velocity of palpebral closure) can be measured over time by physiologic biosensors. If the atypical measured responses persist over a specified time period the electronic interface controller system can be activated to control a vehicular response/equipment response.

Monitoring human quality of function of the abnormal eye movements, eyelid (e.g. palpebral or palpebrae) movements or position(s), vital signs or biochemical biometrics can enable safer control of vehicular operation or operator interface controller systems when human performance is suboptimal. Specifically, while tracking eye movements or eyelid movement, if specific deviant or a relative amount of abnormal eye movements occur over a specific period of time, such as nystagmus, from any one of the various types of nystagmus, or other abnormal responses such as abnormal saccades, abnormal blinking, prolonged eye blinks, abnormal twitching, or jerking, or prolonged eye lid closure (e.g. temporally related abnormal palpebral position) embodiments of this invention can observe such findings and measure the abnormality over a specified time. This tracking of abnormal eye movement and/or eyelid movement and measurement can be performed using videonystagmometry or video camera eyelid sensors. The video camera would measure palpebral movement (e.g. palpebral position) with measurement of the duration of palpebral closure, whether it is temporal involuntary or voluntary eyelid movement. If the time duration for the abnormal tracked movement is reached as being significant, this data can be interfaced with the operational controller system of the vehicle or powered equipment. For example, if a person is operating a vehicle or powered equipment and is falling asleep, then the video camera would be responsive to the prolonged temporal involuntary eyelid movement and trigger an interface controller system. Therefore smaller and brief insignificant eye movements such as routine eye blinks, or saccades might not trigger the electronic interface controller system, but will be seen by the physiologic eye sensor.

Embodiments of the present invention can measure numerous ocular indices including eyelid position detection, eyelid blink rate (palpebrae closure rate), eyelid blink duration (palpebrae closure duration) or temporal involuntary eyelid movement, percentage of eyelid closure (palpebral fissure height, palpebral aperture), marginal reflex distance, frequency of eye blinks, and velocity of eye blinks. The physiologic based sensor can detect a prolonged duration of the palpebrae (eyelids), such as 5 seconds, and this abnormal input value can result in the determination of a controller response. For example, if the opening of the palpebrae is 5 mm, for a specific duration of time (e.g. for example 5 seconds), this abnormal input value would trigger the controller response. This abnormal input value could also include the marginal reflex distance when it is less than 2 mm for a similar time period (e.g. for 5 seconds). This abnormal value for a specific time span could be triggered for any time span by the algorithm.

Since normal vertical height of palpebral fissure is near 10-12 mm in adults, ptosis can be identified when the upper eyelid is less than 2 mm from mid-pupil. When severe ptosis (e.g. 4 mm) is present, this abnormal input value could also be measured by embodiments of this invention and this could trigger the algorithm controller to control vehicular or powered equipment.

Physiologic based biosensors can also measure the relative amount of abnormal physiological biometric responses of the vital signs, such as electroencephalographic changes, blood pressure, pulse changes as well as biochemical characteristics, such as oxygen saturation, glucose, alcohol levels and can include hematocrit and hemoglobin levels. When a relative amount of abnormal measured levels is detected, the physiologic biosensor can interface and control the operational controllers of the vehicle or powered equipment. For example, when the blood alcohol level reaches 0.08 (which is the legal limit for being drunk) the operation of the vehicle can be controlled by the input interface. If the body pH becomes abnormal and reaches 7.35, or the oxygen saturation of an individual falls below 85%, the human performance can decay and the operation of the vehicle or powered equipment can similarly be controlled by the input interface. If an operator has a hypotensive episode with a systolic blood pressure less than 80 millimeters of mercury (mm Hg), or diastolic less than 50 mm Hg, or has significant bradycardia with a heart rate of 50 beats per minute these physiologic based sensors can detect the abnormal values and this input value can result in a controller response. The presence of a hypertensive episode or the presence of delta waves can trigger a similar corrective and alarm response. The physiological biometric tracking and detection of abnormal biometric levels can be the input for the controller response. The algorithm which has been triggered by the physiologic biosensor, and which has detected the relative amount of abnormal physiological biometric value, can be used to control a vehicle or the operation of electrical equipment safely, when the human body characteristics are less than optimal performance to perform specific tasks, such as vehicular operation, or operation of powered equipment. This data can also be actively streamed to a remote or distally located source and the remote source also can interpret the active streaming data and make changes to the vehicular or powered equipment controller. This data can provide an alarm to the operator either auditorially, haptically or visually and can provide remote alarms to the user and/or to the remote source. The auditory alarm can be a variety of types with varied frequencies. The haptic alarm can be in the form of a sensor that vibrates or elicits other somatosensory signals, such as twitches, electrical pulses or other responses. The visual alarm can be in the form of lights, which may have different colors, text information or other visual symbology.

Another embodiment of the invention can be to measure the biological observation of images from retinal scanning, corneal reflection, pupil center corneal reflection or reflections from the iris. The images seen can be the images biologically observed by the eye, and the information seen can be detected by a sensor and recorded and interpreted by a processor. If the data has a pattern compatible with reflected text information, as from a smart phone or similar device, the data can be electronically interfaced with the operational controller system of a vehicle or powered equipment to control safely the vehicular operation or powered equipment. The reflected image detected by the sensor, can lead to a faster vehicular or powered equipment response that what would be produced by an inattentive user or operator. Like the other embodiments, this embodiment can provide an alarm to the operator either auditorially, haptically or visually and can provide remote alarms to the user and/or to the remote source.

In one embodiment the system comprises an eye tracking camera, either worn as eyewear, on contact lens, or with a helmet mounted system. The system can track and/or monitor a relative or specific amount of abnormal eye responses, movements, activity of the operator(s) in the form of nystagmus, eyelid closure, and/or movement of the eyes from the plane of measurement for a defined period of time and/or can detect SMS text (text message) reflections on the cornea or abnormal head movements, such as being out of the plane of required visualization for a defined period of time. For example, it the inattentiveness to operation of the vehicle is detected, the physiologic based eye biosensor detects the abnormal physiologic eye responses, movements, or activity and electronically interfaces with a processor, which processes the information received from the eyes. An algorithm, using the input for the controller response can then alert the operator if abnormal criteria are met and can therefore properly control the vehicle (including aircraft) or powered equipment if the relative amount of defined abnormal criteria are met.

In embodiments of the present invention, haptic sensors can be attached to the eyewear, helmet, skin surface, or can be in contact with the skin surface by being affixed by what is being worn, or in contact with the skin surface by what is adjacent to the skin surface, such as a seat, back of a chair, flooring surface, or other nearby object from which the somatosensory stimulus can occur. When the abnormal physiologic based metrics are detected, the haptic sensors can vibrate, stimulate, pulsate, provide a sense of movement, or send alternating electric currents to the skin causing a somatosensory experience to the user or operator. This somatosensory experience can be detected as an alarm signal by the user or operator and can be sent remotely to another location, as an alarm to others. This can be done in real time. It can be done using active live streaming. Similarly, the remote location can alternatively send a somatosensory experience back to the user or operator.

In embodiments of the present invention, auditory-based sensors can be attached to the eye wear, helmet, or skin surface or can be in contact with the skin surface by being affixed by what is being worn, or in contact with the skin surface by what is nearby to the body, such as a seat, back of a chair, flooring surface, head rest or other nearby sound generating system. When abnormal physiologic based metrics are detected, the auditory sensors can cause an audible sound to be detected by the user or operator. This auditory signal can be detected as an alarm signal by the user or operator and can be sent remotely to another location, as an alarm to others. This can be done in real time. It can be done using active live streaming. The remote location can send an auditory signal or auditory experience back to the user or operator.

The camera or eye tracking camera system can be embedded in the components the operator or user is looking at or looking through or it can be distally or remotely located. Examples of external components that can hold the camera can include the window shield, windshields, computer screens or similar devices. These cameras could track or measure the abnormal eye responses, eyelid movements, prolonged palpebral (eyelid) closure, or movement of the eyes from the plane of measurement for a defined time. These cameras could detect SMS text reflections on the cornea or abnormal head movements, such as being out of the plane of required visualization for a defined time.

The system can incorporate remote physiologic biosensor detection, which can be distally positioned from the user or operator. This remote physiologic biosensor detection could track head movement, head velocity, or abnormal eye movements, or prolonged eyelid closure, physical monitoring and physiologic measurements of the vital signs as discussed previously.

3. Description of the Figures.

Referring now to the figures, FIG. 1 illustrates an exemplar environment 100 that is highly provocative to motion sickness and spatial disorientation: an aircraft. In the example shown there are two crew-members 110 and 120. Each crew-member is equipped with a flight suit 112 and 122, helmets 114 and 124 which may include a helmet mounted display or eyewear display 116 and 126. The crew-members are also equipped with various sensors 130, 132 which monitor various biometric parameters and environmental data. By way of example sensors may include: blood oxygen, pressure, heart rate and other EKG waveform information, respiration rate and gas levels delivered and exhaled. Position of the user's head and trunk (core body); core temperature and skin temperature; limb movement muscle flex/contraction and relaxation; eye movement; EKG parameters; cabin pressure and oxygen and other gas levels; vibration, light levels; aircraft acceleration, speed and position.

These sensors are typically directly or indirectly input into the electronics or avionics 200. The electronics may include central processors system(s) 210 and subsystems 212 and sensor interfaces (not shown separately). Each crew-member also typically has a console 118, 128 which provides the user with the mean to electronically interface with the avionics and electronics to access information and to give instructions. In the illustration the crew members are seated in seats 140 which may be set with rockets or charges for emergency ejection from the aircraft 100. In the illustration shown, both crew members are in a cockpit structure 142 which is fitted with rockets or explosive charges 144 to eject the cockpit as a capsule.

Figure 2:
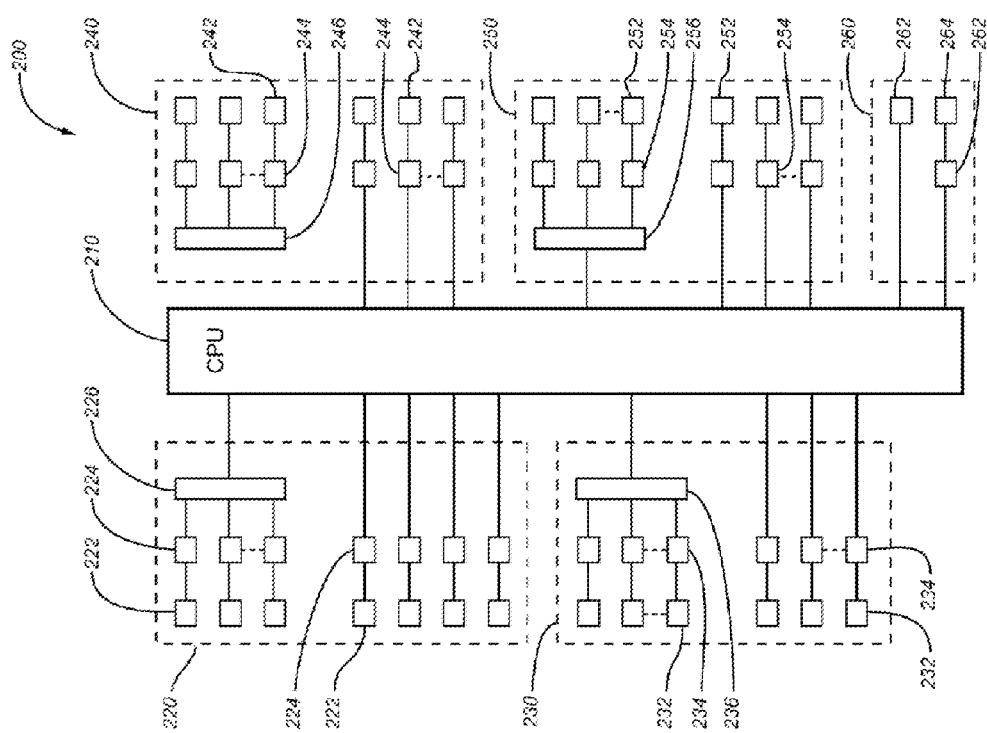
FIG. 2 illustrates an example of major avionics hardware components.

FIG. 2 is an illustration of an example electronics/avionics 200 hardware components. At the center is shown a central processing unit CPU 210 typically a special purpose computer. For the purposes of this illustration the avionics subsystems have been divided into five different types. On the left side are shown the vehicle centric hardware subsystems and on the left side are shown the human centric subsystems. The vehicle centric subsystems have been divided into two groups: the vehicle centric inputs 220 and the vehicle centric outputs 230. On the right side they have been divided into three groups the human centric inputs—passive 240, the human centric inputs active 250, and the human centric outputs 260. The following lists are not intended to be exhaustive but merely to serve as examples.

The vehicle centric inputs may include sensors 222 which may be connected to the CPU 210 via a sensor interface 224 with or without a preprocessor 246. These vehicle centric inputs 220 generally fall into three major categories: control, performance, and navigation. The following are by way of example types of aircraft centric inputs: AHRS (attitude heading reference system) and AAHRS (altitude, attitude, heading reference system) systems which may include instrument settings actuals, which may further include multiple measures. For example altitude may include sea level, hard deck and/or density altitude. Attitude may include pitch bank and yaw; and the heading may be magnetic and/or true. Speed measure may also be captured which may include ground speed, indicated air speed, calibrated and/or true and may include a mach value. Navigational aids may include HSI (Horizontal Situation Indicator, HSI with CDI (course deviation indicators) which may include glide-path/slope deviation. NDB (non-directional or locator beacon systems), TACAN, LORAN, GPS (other locator systems). In addition various landing assistance systems may be used such as: land based ILS (instrument assist landing system); ship based ICLS (instrument assist carrier landing system); GPWS and EGPWS (ground proximity warning systems); TCAS (traffic collision avoidance system); AoA or AoAS (angle of attack systems); ADS-B (air dependant surveillance broadcast); targeting view systems). The inputs may also include performance related measures/sensors such as: cockpit or cabin temperature pressure oxygen vibration component analysis, engine and instrument settings and performance monitoring sensors, yaw damper system setting and performance monitoring systems.

The vehicle centric outputs 230 may include sensors 232 which may be connected to the CPU 210 via a sensor interface 234 with or without a preprocessor 236. For aircraft the vehicle centric inputs 230 may include: Alerting systems which provide the human user information about the status of the aircraft; Auto Pilot which controls flight of the aircraft; GLOC (gravity induced loss of consciousness) systems which activates an auto pilot which controls flight of the aircraft; GPW (Ground proximity warning) systems which alert the human user of breach of a soft deck and in extreme cases invokes an auto pilot which plots a recovery path and takes control of the aircraft. Return home loss of link systems will either take over control of the aircraft and put it into a holding pattern or direct the aircraft to a home (or just a safer location). The vehicle centric output for an aircraft typically would also include output to the onboard flight and munitions delivery system associated with the aircrafts functions such as directing cannon fire or firing, launch and release of rockets.

The human centric inputs passive 240 may include sensors 242 which may be connected to the CPU 210 via a sensor interface 244 with or without a preprocessor 246. These human centric inputs passive 240 may include the aforementioned biometric information and information concerning the human user's environment.

The human centric inputs active 250 may include sensors 252 which may be connected to the CPU 210 via a sensor interface 254 with or without a preprocessor 256. These human centric inputs active 250 may include: manipulation of control devices such as the stick/wheel, pedals and power or thrust controls. It may also include biometric readings such as eye movement which the human user intentionally uses to control flight or targeting systems.

The human centric outputs 260 may include devices 262 which may be connected to the CPU 210 via an interface 264 with or without a preprocessor. These human centric outputs 260 may include: instrument panels or displays which may be in a dashboard configuration and/or a heads up display, or HMD (helmet mounted display; eyewear display; hepatic actuators intended to give hepatic feedback to the human user; EVS systems (enhanced vision synthetic).

It should be understood that though the inputs and outputs have been so divided. Various avionics subsystems may share inputs and outputs. For example the present invention and a targeting system may share the same visual display. Various avionics subsystems may also provide processing—the results of which may provide inputs to other avionics subsystems.

Figure 3:
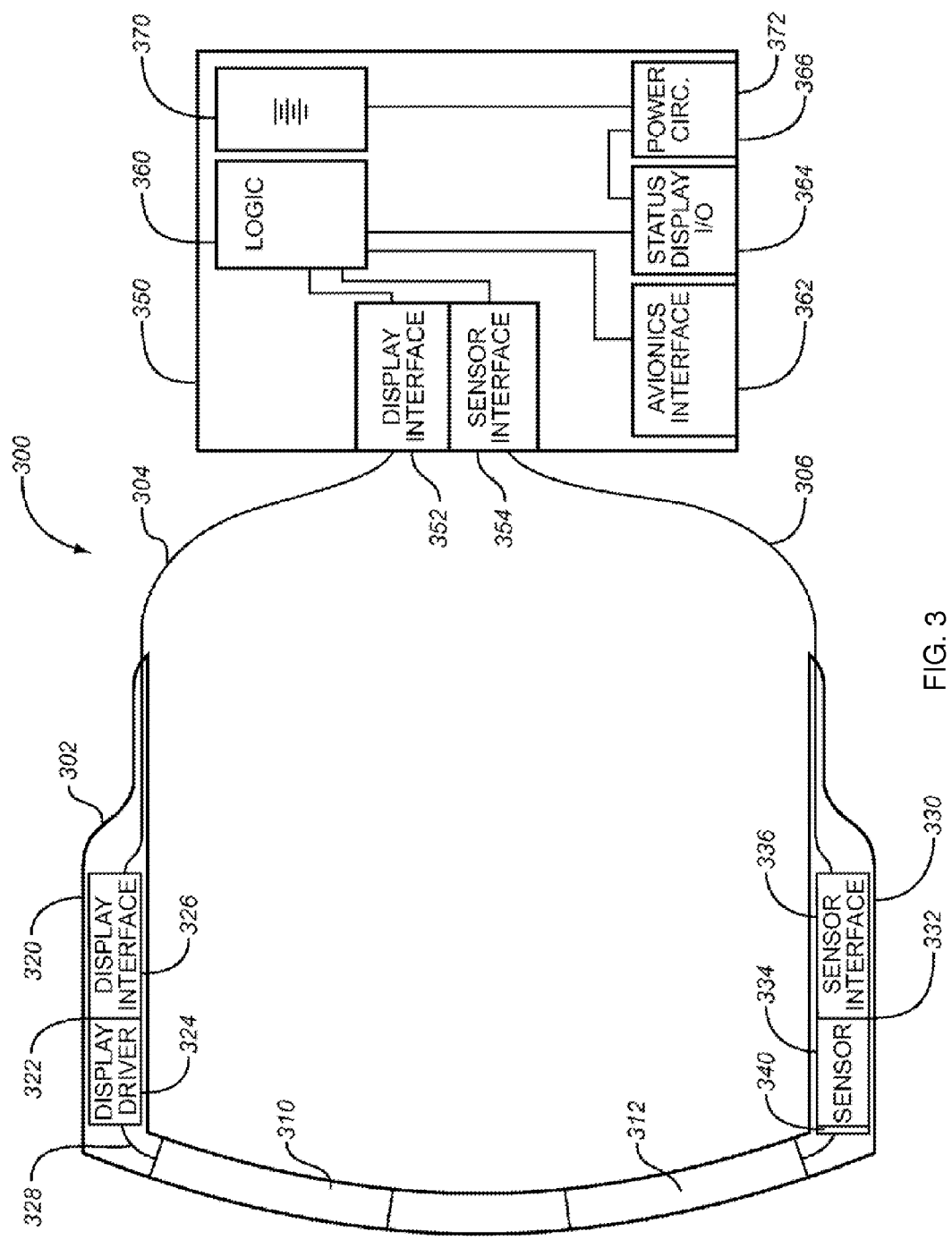
FIG. 3 illustrates a monocular example of an avionics subsystem implementation of the present system.

FIG. 3 is an illustration of major hardware components of an avionics subsystem 300 which has proven to prevent, avoid, ameliorate, and/or quickly resolve/correct SD/MS symptoms. The embodiment illustrated in FIG. 3 takes the form of a pair of eyewear glasses 302 to be worn by the user (not shown) electrically connected 304, 306 to a logic and power dongle 350. The embodiment illustrated in FIG. 3 is of a monocular system: so called because the eyewear has a right lens set 310 which incorporates a digital display and a left lens set 312 which does not. The glasses include a right temple 320 and a left temple 330. The right temple incorporates an electric control and communication circuitry which takes the form of a circuit board 322. In this embodiment the right temple 320 circuitry board 322 includes a display driver 324 for driving the display in the right lens set 310. It also includes display interface circuitry 326 for receiving a display signal from the dongle 350 and generating status information back to the dongle. In the embodiment illustrated the display driver circuitry 324 communicates with the display 310 via an electrical connection 328.

In the embodiment illustrated in FIG. 3 the left temple 330 also incorporates an electronic circuitry which takes the form of a circuit board 332. The circuitry on this circuit board 332 includes sensor circuitry 334 and sensor interface circuitry which communicates with the dongle 350. In some embodiments the sensor interface may include circuitry for doing sensor data preprocessing. In the embodiment illustrated the sensor circuitry includes micro-electro-mechanical system (MEMS) chip(s) (sometimes referred to as micromachines and may sometimes take the form of NEMS (nano-electro-mechanical systems). In the embodiments such as the one illustrated in FIG. 3, the applicant used two chips which sense inertial changes and together provided six degrees of freedom: three degrees representing rotation on three orthogonal axis and three representing inertial changes along each of the three axes. For many applications only three degrees of freedom may be required to gather and track the necessary data to generate the symbology. In a limited set of applications, it may be possible to incorporate aspects of the present inventive system with less degrees of freedom if the environment only provides inertial changes and is limited to a single two dimensional plane rather than a three dimensional space. In successful embodiments manufactured by the applicant, inertial sensors that detected both gyro type and accelerometer type of inertial sensors are used. Sensor data pre-processing circuitry; and a micro-electro-mechanical system are used in an integrated circuit wherein the micro-electro-mechanical system further is comprised of an accelerometer.

In the embodiment illustrated in FIG. 3, the dongle 350 includes communications circuitry, logic circuitry and power management circuitry. Those skilled in the art will appreciate that in an implementation of the embodiment illustrated in FIG. 3 two or more circuit boards can be employed: communications and logic on one board and power management on a second. The circuitry includes communications interface circuitry 352 and 354 for communications with the sensor board 334 and display driver 324 via communication links 304 and 306. The communications interfaces 326/352 and 336/354 interface communications with a central logic processor 360. The logic processor processes the sensor data from the sensors 340 and generates graphics information to be displayed on the display 310. Though not shown, the logic processor employees firmware programs and/or memory unit for storing software programs. The logic circuitry also has access to an avionics communications interface 362 to get information from other avionics systems/subsystems and sending information to the avionics systems/subsystems.

The dongle 350 also includes power management circuitry 366 which receives power from a charging port 372 and which manages and distributes power to charge a battery 370 and for use by all components/boards requiring electric power. The power circuitry 366 is also connected to status display circuitry 364. The status display circuitry 364 is also connected to communicate with the logic circuitry 360.

Figure 4:
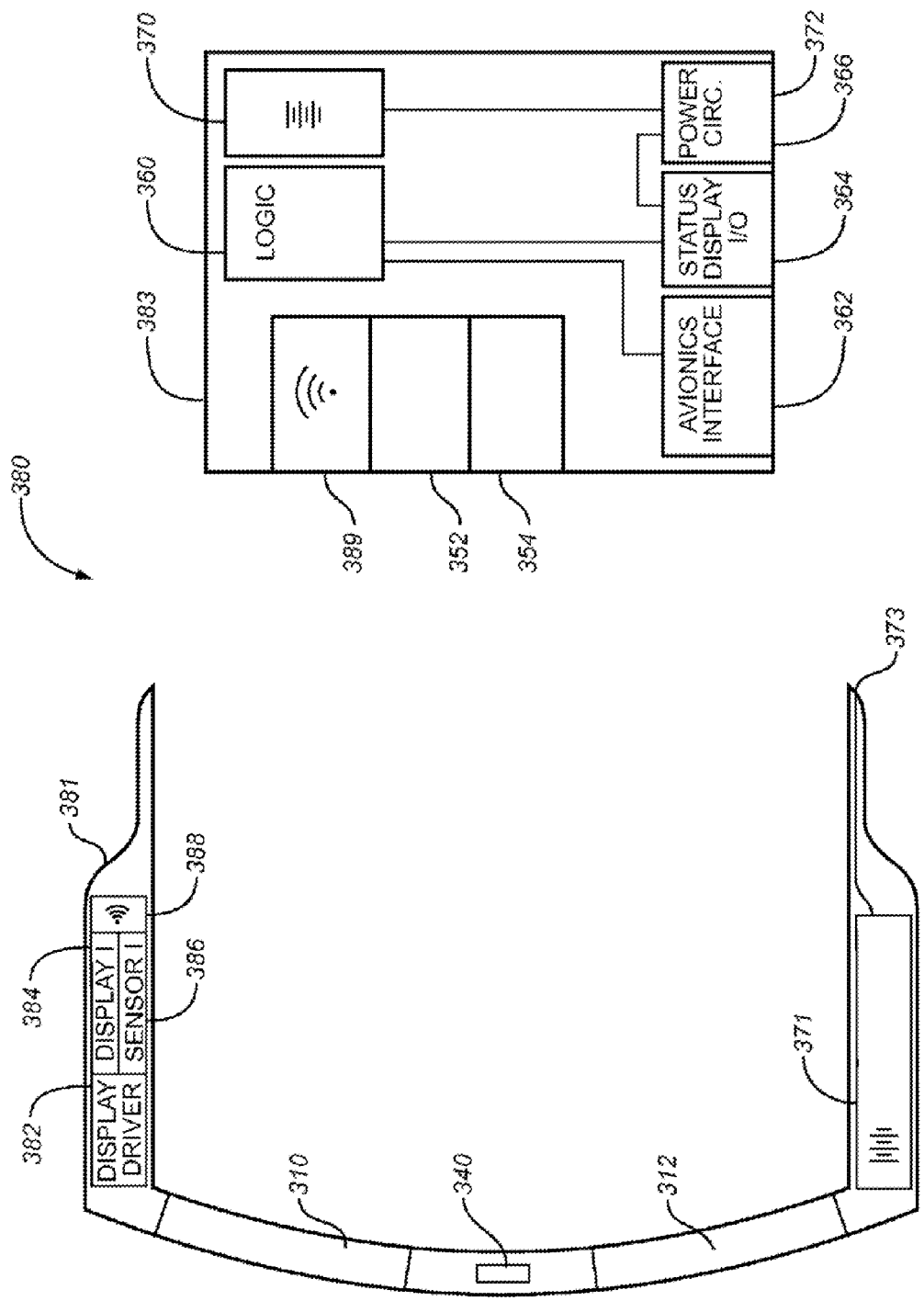
FIG. 4 illustrates an alternative embodiment of an avionics subsystem implementation of the present system.

FIG. 4 illustrates an alternative embodiment 380 of the avionics subsystem. This embodiment employs a display in each lens set 310 and 311. This embodiment may be employed in either monocular or binocular modes. In monocular mode, graphics are displayed on only one display 310 or 311 and presented only to one eye as with the embodiment 300 in FIG. 3. In binocular mode graphics are displayed on both displays. In binocular mode the same graphics may be displayed to both eyes or different information can be presented to each eye. In binocular mode it is possible to project the graphics as a three dimensional image by presenting each eye with different information and using different depths of field for the information displayed, if desired.

In embodiment 380 the driver(s) for both displays 382 are located on one temple side of the headset 381. In embodiments where a binocular mode presents the same information to each eye only one display driver is necessary. If the displays do not present the same information multiple display drivers may be necessary. In embodiment 380 the inertial sensors 340 are mounted in the bridge of the headset 381 which would present over the nose between the eyes of the user. In this embodiment the sensors circuitry also resides on the same temple side of the headset 381 as the display driver 382.

The embodiment 380 in FIG. 4 also differs from the embodiment 300 in FIG. 3 in that embodiment 380 includes wireless communication link 388 and 389 between the head set 381 and the dongle 383. A myriad of wireless communication links are suitable: such as blue tooth for example. A battery or batteries 371 reside in the opposite temple side of the head set. The battery can be charged via a charging port 373. The battery charging and conditioning circuitry reside in the charger (not shown). The batter(ies) 371 and inertial sensors 340 are electrically connected to the display driver 382, display driver interface 384, sensor circuitry 386 and headset wireless com 388 via electrical conductors (not shown) in the frame of the headset 381.

Figure 5:
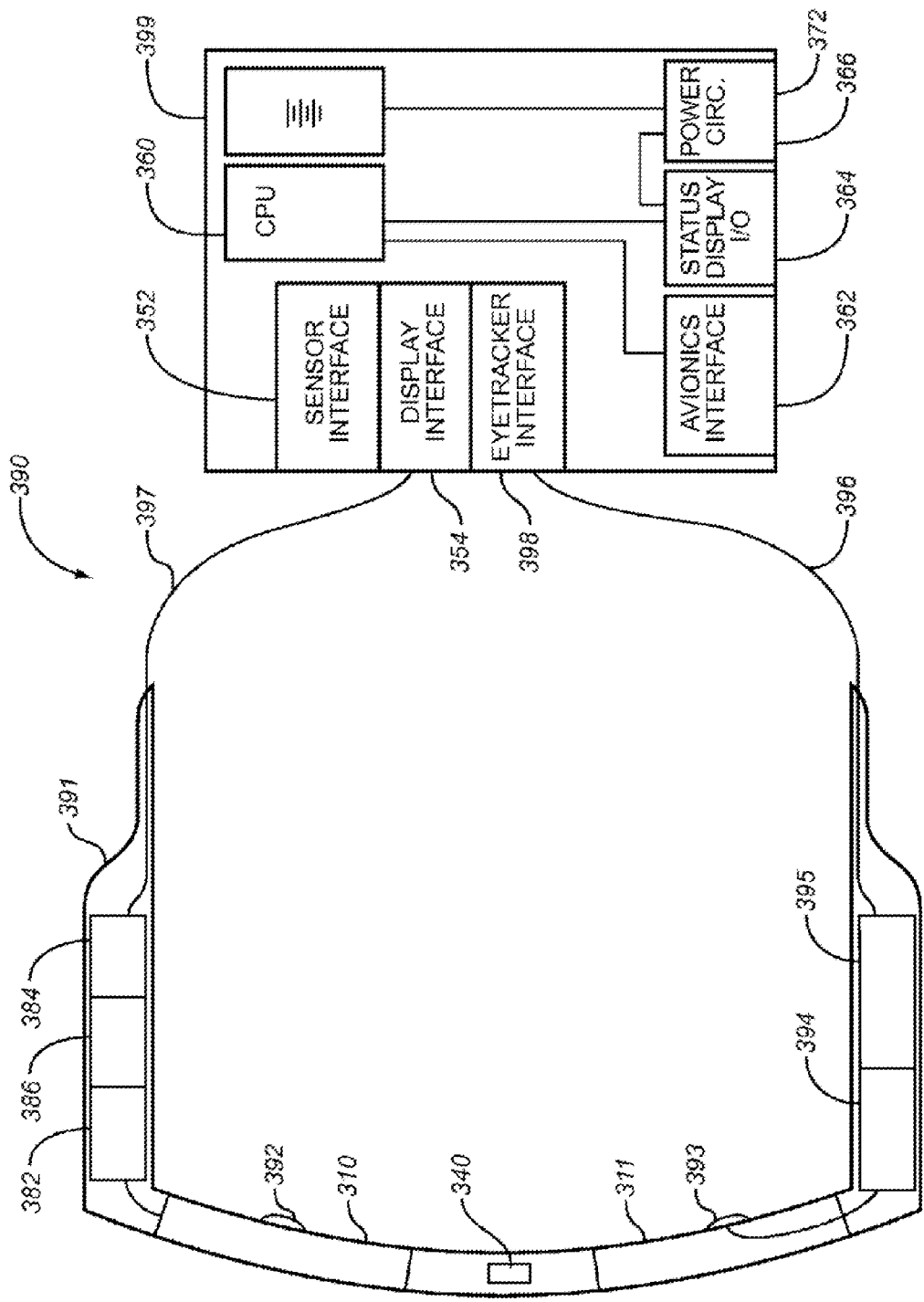
FIG. 5 illustrates a binocular alternative embodiment of an avionic subsystem implementation of the present system.

FIG. 5 illustrates yet a further embodiment 390 of an eyeglass headwear 391 implementation of the avionics subsystem. This embodiment further employs the use of eye sensors 392, 393. In one embodiment these sensor 392, 393 take the form of video cameras, which records images of the user's eyes as they move during use of the system. The video cameras are controlled by camera driver circuitry 394 and video interface circuitry 395 which interfaces with video interface circuitry 398 in the logic/power dongle 399 via umbilical electrical connection 396. The logic circuitry in the dongle 399 monitors ocular parameters like eye vertical (up and down) and horizontal (left and right), combined vertical and horizontal, and rotational eye movement and pupil dilation. This embodiment also includes inertial sensors 340 in the bridge of the headwear 391 and associated sensor circuitry 386 and interface circuitry 384 for interfacing with the logic and power dongle 399 via electrical connection umbilical 397. The embodiment also includes two displays in lens sets 310, 311, which are driven by video driver(s) 382 and interface with the logic/power dongle 399 with interface circuitry 384 via electrical connection umbilical 397.

Figure 6:
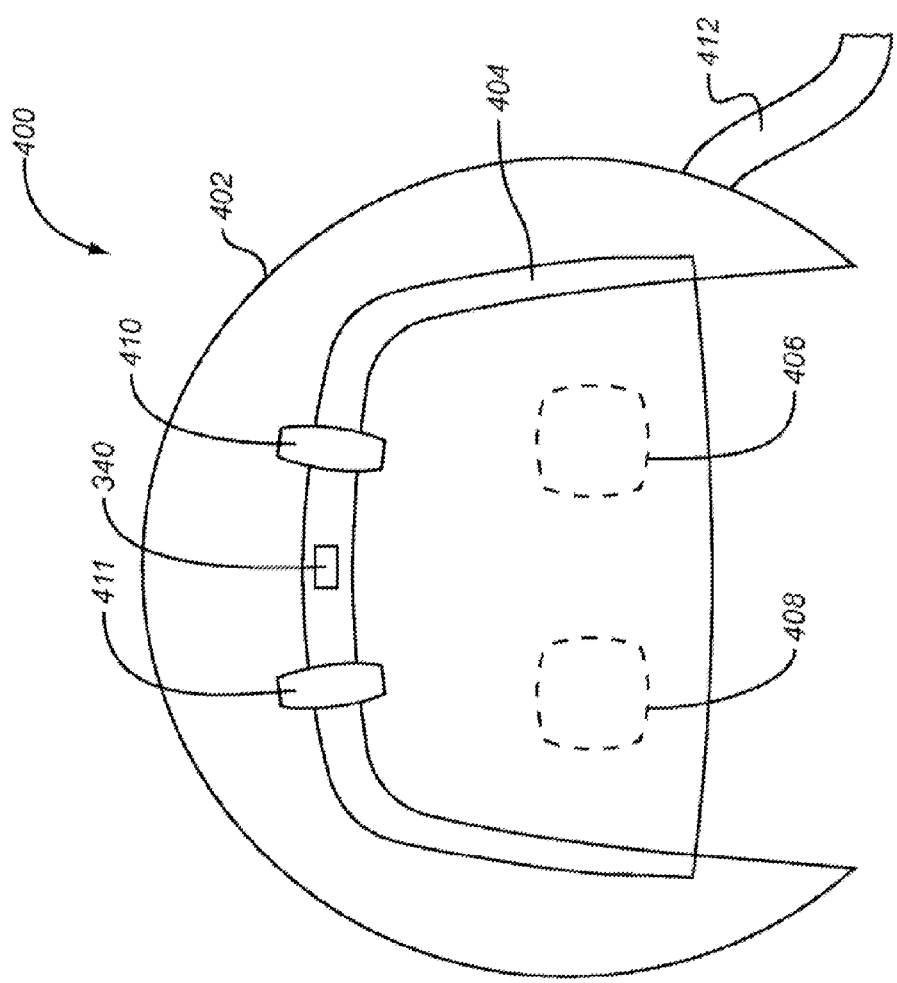
FIG. 6 illustrates a HMD alternative embodiment of an avionic subsystem implementation of the present system.

FIG. 6 illustrates a HMD (helmet mounted display) embodiment 400 of the headwear portion of an avionics subsystem. This embodiment includes a helmet 402 with a visor 404 onto which data can be displayed in display regions 406 and 408. The helmet 402 is also configured with eye sensors 410 and 411 which track ocular parameters such as pupil size and eye movement. The inertial sensors 340 are also helmet mounted. The element connected to the other avionics systems and subsystems via an umbilical 412 that contains electrical and optical conduits (not shown) for communication. For avionics applications of the user stabilization system taught herein, the HMD embodiment of the headwear portion of the subsystem is preferable for fighter applications such as for the 5th Generation Fighters where helmets are traditionally used. The eyeglass embodiments illustrated in FIG. 3, FIG. 4 and FIG. 5 may be better suited for what is sometimes called shirt-sleeve environment applications: both airborne and terrestrial.

Figure 7:
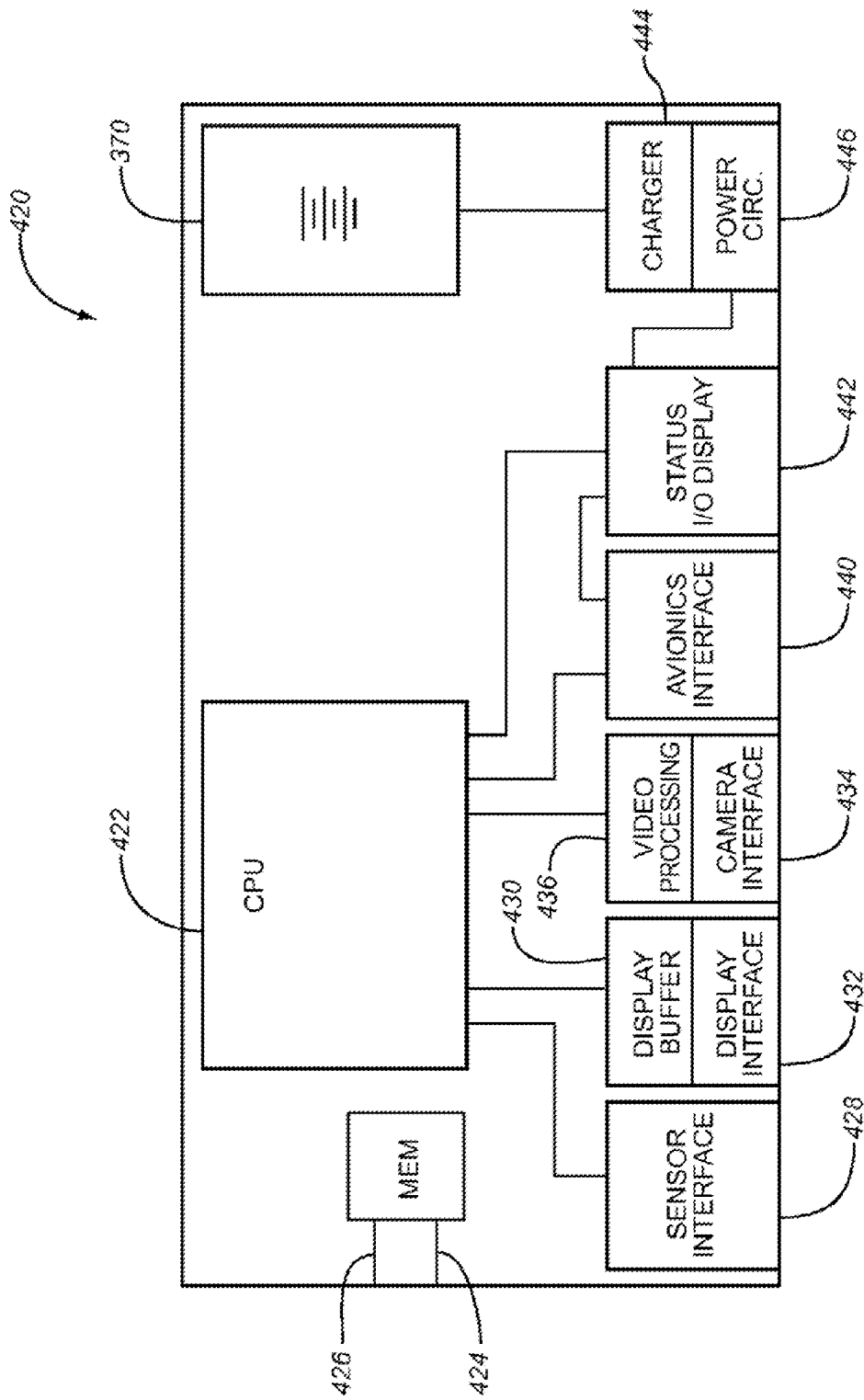
FIG. 7 illustrates an embodiment of an implementation of a logic dongle.

FIG. 7 illustrates an embodiment of a logic and power dongle 420 which may be used with the HMD. The dongle includes a central processor 422 which has access to memory 424 on which programs are stored. In alternative embodiments the programs may be hard coded into the hardware processor. However, in the embodiment shown the programs are downloadable via a programming link 426. The CPU 422 receives information from the inertial sensor interface 428 and the avionics interface 440. The CPU provides output to the display interface 432 which includes a display buffer 430 and the avionics interface 440. CPU 422 also receives information from a video image processor 436, which processes digital video images of the user's eye(s) via the digital camera interface 434. To a limited extent the CPU 422 also provides output to the sensor interface 428 for calibrating and resetting the sensors. The CPU 422 also receives and sends information to the status display 442 which also includes user inputs (not shown) for turning on the power and resetting/calibrating the inertial sensor circuitry. The dongle 420 also includes power control circuitry for receiving monitoring distributing electric power which includes battery charging circuitry 444 for charging a system battery 370.

In a further embodiment the logic and power dongle 420 may be incorporated in the helmet in which case the battery 370 and battery charger circuitry 444 may not be necessary since power will be supplied through the HMD umbilical.

Figure 8:
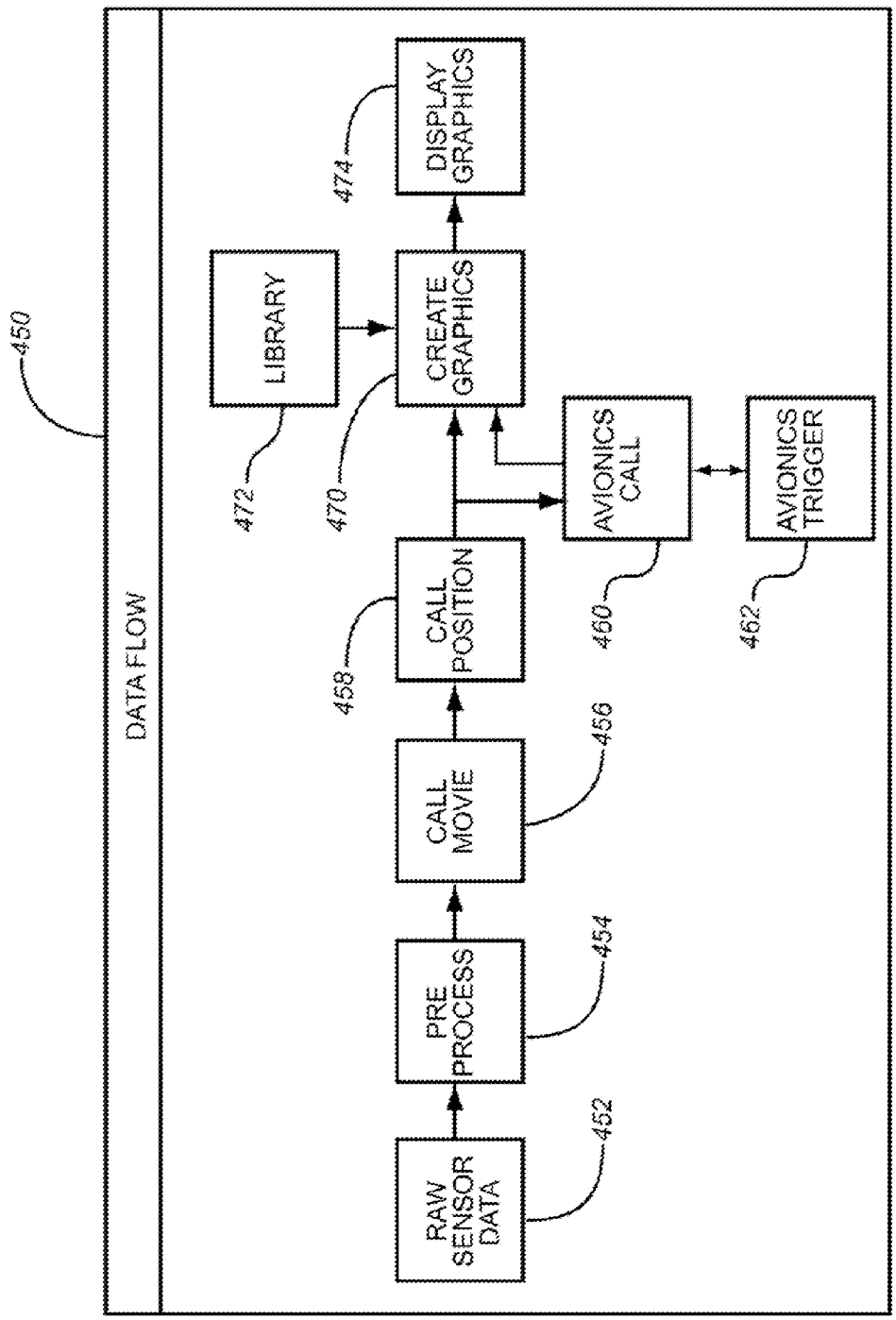
FIG. 8 illustrates an embodiment of data flow in the avionics subsystem.

FIG. 8 illustrates the data flow 450 of the avionics subsystem. In this illustration data flow 450 begins with the raw data generated by the inertial sensors 452. The sensor generated raw data 452 is extracted by and preprocessed into digital form 454. The digital data is further processed to calculate acceleration from which both movement and position are calculated 456, 458. This information is then further processed 460 in combination with information from other avionics subsystems 462 to generate the information needed to generate the graphics 470 using a graphics library 472 to be displayed 474 to the user.

FIG. 9 illustrates in greater detail and embodiment o the display lens sets 310, 311 (not shown). This embodiment 310 contains three components 490, 492 and 494. The central components 490 are digital displays. A myriad of display technologies are suitable for different applications. Examples of such technologies include but are not limited to light emitting diode (LED), organic light emitting diode (OLED), Flexible OLEDs and liquid crystal on silicon (LCOS) and wave guide array technologies or other displays such as low temperature Poly Silicon (LTPS) and excimer laser annealing (ELA) displays. Different applications may call for different choices of display technology. The factors to consider are the pixel size, the lumen output, the efficiency or power required to achieve the desired lumen output. For avionics requiring daytime usage a higher light output is necessary. Therefore for such an embodiment the applicants found an arrayed waveguide display (AWD) to be particularly suitable to obtain a suitable lumen output with adequate resolution in a eyeglass mounted display.

The outer lenses 492 and 494 combine to create the desired focal plane for the display. In the preferred embodiment the desired focal length for the display is approximately two to three feet or about a meter. In other embodiments, other focal lengths can be used up to infinity (focal lengths of about fifteen to twenty (15-20) feet and beyond serve as effectively infinity for the human eye). It is preferred that the mating surfaces 493, 491 and 497, 495 match to reduce the internal reflect between the components and so that if desired the components can be adhesed/glued together to further reduce internal reflections within and between the components. The embodiment illustrated in FIG. 9 employs flat mating surfaces 493, 491, 497, 495. This has been found to allow for relatively thin lenses. In this embodiment of a lens set it is possible to account for user specific vision correction by shaping the user facing surface 498 to the inside lens 494. In alternative embodiments other shaped mating surfaces may be employed. In further embodiments the display may be manufactured in a substrate which is thick enough to be ground so that the lens set is comprised of a single lens. In further embodiments it might be desirable to include thin film coatings on the lenses which would optimize their use in particular conditions such as night vision, in daylight or prescription requirements.

Symbology. Of critical importance to success of the system is the symbology of the cues provided to the user to prevent, avoid, and ameliorate spatial disorientation and motion sickness. Not only is the information provided important but experience demonstrates that how the information is provided is critical to successful use of the system. The following describe embodiments of symbology that has been demonstrated to be successful. Many factors are important to the success of the cue symbology such as, shape(s), color(s) and dynamic mechanization(s) of the symbology as used in various embodiments for various applications.

The particular combinations of symbology and symbology elements and functions may vary. The variety may in whole or in part be driven by the application in which the embodiment is intended for use. For example symbology appropriate in particular medical or other military applications are likely to differ from symbology appropriate for aviation applications. With even more granularity different symbology may be appropriate for two different medical applications. Similarly different symbology may be appropriate for two different military applications such as driving a jet fighter verses flying a drone remotely or driving a tank. Nevertheless some of the features are common.

Head-Attitude Scale (HAS). An embodiment of a head-attitude scale (HAS) 510 with in a Field of View (FOV) 508 is illustrated in FIG. 10. In some embodiments, the HAS 510 is a magenta-colored Cartesian graph with equal-length x-(horizontal) axis 512 and y-(vertical) axis 514 that intersect in their respective centers at the graph origin (vertex) 516. In some embodiments the HAS 510 is centered in, and extends to the limits of, the display field-of-view FOV 508 as depicted in FIG. 10.

In this embodiment, the horizontal axis 512 represents a range of plus or minus One Hundred and Eighty degrees (±180°) of lateral rotation (yaw) from the vertex 516 and is not indexed. The vertical axis 514 presents a range of plus or minus plus or minus Ninety degrees (±) 90° of vertical rotation (pitch) and has four short indices 518, 522 and 520, 524 respectively representing plus or minus Forty-Five degrees ±45° and plus or minus Ninety degrees ±90° pitch displacement from the vertex 516. In this embodiment, the vertical axis 514 extends past the useable scale plus or minus Ninety degrees (±90°) 520 and 524 in order to provide continued visual stimulation and stability in the vertical plane to the limits of the FOV 508. No symbols are displayed above or below the plus or minus Ninety degrees ±90° indices on the HAS 510 vertical axis 514.

Pitch/Roll Indicator (PRI). An embodiment of a Pitch/Roll Indicator (PRI) 530 is illustrated in FIG. 11 and FIG. 12. In some embodiments this indicator is a tangerine-colored line with a length approximately one-third the length of the HAS 510 horizontal axis 512. The PRI 530 is bisected by, moves vertically along, and rotates (tilts) about the HAS 510 vertical axis 514. Consequently, the PRI 530 represents the pitch and roll attitude of the users head relative to the real-world horizon and as referenced against the HAS 510.

FIG. 13 and FIG. 14 illustrate an alternative and in many cases preferred embodiment of the Pitch/Roll Indicator (PRI) 530 is comprised of two perpendicular lines 531 and 534 with the shorter of the two lines 534 placed on top and in the center 532 of the longer line 531. In this embodiment the longer line (pitch/roll bar) 531 is of the same dimensions as the as the PRI in FIG. 11 and FIG. 12 and is oriented the same relative to the HAS 510 vertical axis 514 to indicate head displacement in the pitch and roll axis. The shorter line (vertical fin) 534 presents the direction toward the top of the user's head and can be considered to point in the direction of the lift vector of an aircraft when the wearer is sitting upright in the seat. In this embodiment, the vertical fin's 534 height is approximately one-ninth the length of the roll bar 531.

In this embodiment the PRI 530 is tangerine-colored when roll attitude is less than or equal to plus or minus Ninety degrees (±90°) as referenced to the HAS 510 vertical axis 514 and red colored when roll attitude is greater than plus or minus Ninety degrees (±90°).

In the embodiments illustrated in FIG. 11, FIG. 12, FIG. 13, and FIG. 14, the PRI 530 is an "outside-in" presentation and represents the wearer's head position as if viewed from a distance from (or outside) the head. For example, head tilt to the right is presented as a right-tilted PRI 530 in relation to the vertical axis 514 of the HAS 510 (i.e. vertical fin 534 "points" to the right of the vertical axis 514). Similarly, an upward tilt of the head is displayed by positioning the PRI 530 on the positive side of the HAS 510 scale relative to the horizontal axis 514 as illustrated in both FIG. 12 and FIG. 14.

In both illustrated embodiments, the PRI 530 rotation is conformal to the real-world (outside scene) in roll, but not in pitch. For example, Thirty degrees (30°) of rotation to the right is displayed as Thirty degrees (30°) roll, while PRI elevation (climb) and depression (dive) are compressed. In other embodiments the angular range of view may differ as may the compression ratio. In yet other embodiments the compression ratio may not be linear. In both models the PRI is limited vertically when it reaches the plus or minus Ninety degrees (±90°) index on the HAS. Some embodiments rotate a maximum of One Hundred and Eight degrees (180°), while the other embodiments may rotate Three Hundred and Sixty degrees (360°).

Head-Rotation/Yaw Indicator (HRI). An embodiment of a Head-Rotation/Yaw Indicator 540 is illustrated in FIG. 15 as an open-ended, three-sided trapezoid. In an actual embodiment the HRI 540 is tangerine-colored.

As illustrated in FIG. 16, the HRI 540 "slides" the length of the PRI 530 as the user's head is rotated left or right of straight ahead about the central axis of the user's head. In the embodiment illustrated, the HRI 540 extends above and below the pitch/roll bar 531 of the PRI 530, but its height is less than the height of the vertical fin 534. The center of the HRI trapezoid remains coincident with the center of the PRI 530 roll bar 531 during pitch changes, while it moves independently along the PRI roll bar 531 when the wearer's head position changes in lateral rotation. The lateral position of the HRI remains constant as long as the wearer's head is rotated away from straight ahead in relation to his or her body.

In alternative embodiments the HRI also represents the rotational position of the users head relative to his trunk. In avionics applications this latter embodiment has proven to be more effective for some users.

Upright/Inverted (UI) Triangles. An embodiment of upright/inverted indicators (UI) are triangles 550 on the ends of the HAS 510 horizontal axis 512. To indicate upright, the triangles 550 are green in color, and the apexes point upward as shown in FIG. 17. Upright is determined by the PRI 530 indicating less than or equal to ±90° of roll as referenced to the HAS 510 vertical axis 514. When roll is greater than ±90°, the triangles change color to red, and the apexes point downward, indicating inverted as shown in FIG. 18.

Focal Length. As previously described, the preferred embodiment the display of the symbology suite focused at a range of approximately two (2) feet in contrast to 15 feet/infinity. Testing revealed this focal length made the symbology more effective in controlling SD/MS and provided a recognizable contrast in symbology from the flight control and fire control targeting symbology associated with HMD and HUD displays.

Colors. The colors cited above where selected based on a particular avionics application. The colors were selected both for their visibility and so that they do not conflict with other symbology presented to the user by other avionics subsystems such as a targeting system. In other applications other colors may be desirable. For example for systems employed for particular use in the dark such as night time, it may be desirable to use green colors in order to maintain night vision. In further embodiments the focal lengths may vary with the symbology. For example, some symbology may be displayed at different focal lengths than other symbology.

Offset Vs. Bore Sight Display. In some embodiments, the location of the symbology within the field of view is programmable. For example, the location of the symbology may be offset from the center bore sight to allow the user to better see through the display and to enhance compatibility with other optical displays such as HMD or night vision equipment and symbology such as fire control targeting symbology. In one embodiment the symbology is presented off bore sight up Ten to Fifteen degrees (10-15°) and left about Thirty to Forty-Five degrees (30-45°) to one side or the other (preferably to the left for the left eye or to the right for the right eye. When the symbology is displayed off bore sight, it is shrunk to fit. In some embodiments, the symbology can still however be set on bore-sight taking the same view-space of his other instruments if desired by the user.

In further embodiments the symbology remains off bore sight during normal operation. However if the avionics sensors experiencing triggering events that suggest that the pilot has begun to experience or may begin to experience spatial disorientation, the symbology increases in size as it moves from off bore sight to on bore sight. In such events, other parameters of the symbology may also be enhanced such as the thickness and color or color intensity. In some embodiments the enhancement may be escalated as the indications of spatial disorientation increase for potential to actual to loss of control. In some embodiments, as the situation escalates, other symbology presented to the user may be overridden to give the user a chance to reorient with out the disorienting stimulation of the other symbology. For example, if the pilot is experiencing nystagmus the fire control targeting symbology may be removed in favor of the reorientation symbology described herein. In further embodiments the user is provided with the option to declutter or deescalate the enhancement of the symbology presentation to the user.

Monocular Display. A avionics subsystem with a monocular display has shown to be effective in controlling SD/MS while reducing power requirements and the size of visual "real estate" required on our glasses and HMD displays. This design also allows for reduced pixilation and computational requirements enhancing reliability and miniaturization. It can be presented in a binocular display if required.

3-D Display. The unique display technology created by the video engine and optics allows for the presentation of a 3 dimensional display if needed or desired and facilitates the interface with other human performance improvement technologies.

3. Eye Tracking.

As previously described, the eye tracking sensors employed in embodiments of the present invention can use video cameras. They can use programs to process the images taken from the video cameras to look for certain types of eye movement characteristics. For example, eye tracker programs can look for eye closure rates and duration of eye closure, which are indicative of spatial disorientation, GLOC or other causes of user disabilities. The programs can also look for abnormal eye movements indicative of nystagmus, which is highly indicative of spatial disorientation. The system can detect both linear (vertical horizontal or between vertical and horizontal) and torsional nystagmus. These detections can then shared with and integrated with vehicular or powered equipment control systems.

Eye tracking is the process of measuring either the point of gaze (where one is looking) or the motion of an eye relative to the head. An eye tracker is a device for measuring eye positions and eye movement. Eye trackers can also be used to measure the palpebral opening, or eyelid position or movement activity. The video camera based eye tracking sensors employed in embodiments of the invention can be used to track various types of nystagmus, abnormal twitching, jittering eye movements, abnormal eye blinks, prolonged eye twitching, saccadic eye movements, prolonged eyelid closure, eyelid position, and palpebral opening size and fixations. The eye tracker programs can look for abnormal eye movement responses indicative of motion sickness, spatial disorientation, dizziness, sensory conflict or sensory mismatch disorders, changes in level of orientation, changes in consciousness, changes in attention state, inattentiveness, and drowsy states.

Eye tracking data can be collected using a contact lens, an eye worn device, a remote system, or ahead-mounted 'eye tracker system. An eye tracker system can include a light source and a camera. The eye tracking system can be used with or without a light source. The light source can be infrared and can be directed toward the eye or eyes. The camera can be used to track the reflection of the light source and visible ocular features such as the pupil. The data from the eye tracking system can be used to measure the movement features of the eyes or eyelids or rotation of the eye, velocity of the eye movement, duration of the eyelid closure, rate of the eyelid closure, and the direction of gaze. Additional information such as blink frequency and changes in pupil diameter can also be detected by the eye tracker. Abnormal values can trigger an algorithm, alarm, and/or controller system for a vehicle or powered equipment. Aggregated eye tracker data can be written to a file for later analysis. Eye tracker data can be used to analyze the visual path of one or more participants across an interface such as a computer screen. In this case, each eye data observation is translated into a set of pixel coordinates. From there, the presence or absence of eye data points in different screen areas can be examined. This type of analysis is used to determine which features are seen, when a particular feature captures attention, how quickly the eye moves, what content is overlooked and virtually any other gaze-related question. Graphics are often generated to visualize such findings. In a variant, eye position is extracted from video images. In another variant search based on an electrooculogram may be used. When using a video-based eye trackers, the camera can be focused on one or both eyes and used to record eye movement as a viewer looks at some kind of stimulus. In one embodiment the eye-tracker uses the center of the pupil and infrared and/or near-infrared non-collimated light to create corneal reflections (CR). The vector between the pupil center and the corneal reflections can be used to compute the point of regard on surface or the gaze direction. A simple calibration procedure of the individual is usually needed before using the eye tracker of this embodiment.

When using an eye-tracking camera, two general types of eye tracking techniques can be used: Bright Pupil and Dark Pupil. The difference between these eye-tracking techniques is based on the location of the illumination source with respect to the optics. If the illumination is coaxial with the optical path, then the eye acts as a retro-reflector as the light reflects off the retina creating a bright pupil effect similar to red eye. If the illumination source is offset from the optical path, then the pupil appears dark because the retro-reflection from the retina is directed away from the camera. Bright Pupil tracking creates greater iris/pupil contrast allowing for more robust eye tracking with all iris pigmentation and greatly reduces interference caused by eyelashes and other obscuring features. It also allows for tracking in lighting conditions ranging from total darkness to very bright. But bright pupil techniques are not effective for tracking outdoors as extraneous IR sources interfere with monitoring. In embodiments of the present invention, eye tracking might typically use a sampling rate of at least 30 Hz. Typical sampling frequencies can include 50/60 Hz, 240 Hz, 350 Hz, and 1000/1250 Hz. The higher sampling frequencies are needed to capture the detail of the very rapid eye movement during reading, or during studies of neurology.

Eye movement information from the eye tracker can be is typically divided into fixations and saccades, when the eye gaze pauses in a certain position, and when it moves to another position, respectively. The resulting series of fixations and saccades can be called a called a scan path. Most information from the eye can be made available during a fixation, but not during a saccade. The central one or two degrees of the visual angle (the fovea) can provide the bulk of visual information; the input from larger eccentricities (the periphery) is typically less informative and analysis algorithms can be structured accordingly. Hence, the locations of fixations along a scan path show what information loci on the stimulus were processed during an eye tracking session. On average embodiments of the present invention are designed to accurately capture fixations that last for around 200 ms during the reading of linguistic text and 350 ms during the viewing of a scene. Preparing a saccade towards a new goal takes around 200 ms.

Scan paths are useful for analyzing cognitive intent, interest, and salience. Other biological factors (some as simple as gender) may affect the scan path as well. As a participant looks at a page on the internet, the eye-tracking device can focus on the pupil of the participant's eye and determine the direction and concentration of the participant's gaze. In one embodiment, the software can then generates data about these actions in the form of heat maps and saccade pathways. Heat maps represent where the visitor concentrated their gaze and how long they gazed at a given point. Generally, a color scale moving from blue to red indicates the duration of focus. Thus, a red spot over an area of your page might indicate that a participant, or group of participants, focused on this part of a page for a longer time. Saccade pathways trace the eye's movement between areas of focus. The movement is not unlike watching a hummingbird move between flowers—there are periods of attention and then rapid movement. A red circle may indicate the area of focus, while a red line indicates the flight.

One attractive capability of the eye tracking technology disclosed here is eye movement analysis, which can provide valuable insight into users' overt visual behavior and attention. It is essential to recognize, however, that without further analysis, raw eye tracking data is practically useless. The most common method for determining the location of a user's observable visual attention is by identifying the fixations and saccades that best indicate where they are focusing on the stimulus in front of them.

A linear filter may be used when processing eye-tracking data to approximate eye movement signals, at least well enough to recognize a pattern. The salient eye movements that are typically identified by eye movement analysis are fixations, saccades, and smooth pursuits. Fixations are a result of one's desire to maintain gaze on a specific, stationary object. Smooth pursuits are similar except for the object of interest is in motion. Saccades represent a voluntary shift of focus from one fixation point to another.

In embodiments of the present invention, saccades can be detected by two means as well: the position variance method and the velocity detection method. The position variance method identifies saccades as those moments in the signal in which the position of the eye changes rapidly. The velocity detection method uses an empirically determined velocity threshold. If the velocity of the signal is calculated as higher than the threshold, it is a saccade. Similarly, if it is below the threshold (as discussed above) it is a fixation. For both fixations and saccades, the velocity method is becoming more widely used because it is more suitable for real-time applications.

Beyond the analysis of visual attention, eye data can be examined to measure the cognitive state and workload of a participant. Some techniques have been validated in multiple contexts as a reliable indicator of mental effort. Driving a car, reading a magazine, surfing the internet, searching the aisles of a grocery store, playing a video game, watching a movie or looking at pictures on your mobile device are such applications of eye tracking With very few exceptions, anything with a visual component can be eye tracked. People use their eyes almost constantly, and understanding how the eyes are used has become an extremely important consideration in research and design.

As noted previously, embodiments of the present eye tracking system can track based on using light reflected by the eye, on the cornea or further in the eye. Whether using an external source or ambient light, some of the techniques for tracking the eye include: limbus tracking, pupil tracking, Purkinje image tracking, corneal and pupil reflection relationship, corneal reflection and eye image using an artificial neural network and.

Regarding lumbus tracking, the limbus is the boundary between the white sclera and the dark iris of the eye. Because the sclera is (normally) white and the iris is darker, this boundary can easily be optically detected and tracked. The lumbus tracking technique is based on the position and shape of the limbus relative to the head. This means that either the head must be held still or the apparatus must be fixed to the user's head. Due to the occasional covering of the top and bottom of the limbus by the eyelids, it is more helpful for precise horizontal tracking only.

Regarding pupil tracking, this technique is similar to limbus tracking. The difference is that in pupil tracking the smaller boundary between the pupil and the iris is used instead of the boundary between the white sclera and the dark iris. Once again, the apparatus must be held completely still in relation to the head. The advantages of this technique over limbus tracking is that the pupil is far less covered by the eyelids than the limbus, and thus vertical tracking can be accomplished in more cases. Also, the border of the pupil is often sharper than that of the limbus, which yields a higher resolution. The disadvantage pupil tracking is that the difference in contrast is lower between the pupil and iris than between the iris and sclera, thus making border detection more difficult.

Regarding Purkinje image tracking, when (infrared) light is shone into the user's eye, several reflections occur on the boundaries of the lens and cornea. These reflections are called Purkinje images. The first Purkinje image is also called the glint, and this together with the reflection of light off the retina—the so-called bright-eye-can be video-recorded using an infrared sensitive camera as a very bright spot and a less bright disc, respectively. When the eye is panned horizontally or vertically, the relative positioning of the glint and the center of the bright-eye change accordingly, and the direction of gaze can be calculated from these relative positions. The problems associated with this technique are primarily those of getting a good view of the eye; lateral head movement can put the video image of the eye out of focus, or even make the image of the eye fall out of view of the camera. Due to the lack of contrast, the center of the iris can be tracked instead of the center of the pupil Regarding pupil and pupil reflection relationship tracking, eye trackers can combine a camera with an infra-red light source that illuminates the eye with bursts of invisible infrared light. Some of this infra-red light disappears into the pupil (the dark opening in the center of the iris), and some of it bounces back off the iris (the colored part of the eye), the cornea (the clear part at the front of the eye), the eyelid or the surrounding skin. All these different areas reflect different amounts of infra-red light, which is picked up by the camera. By analyzing the reflections using "a lot of very fancy matrix math" it is then possible to work out where the eye is pointing. Because eyes move in tandem, this only needs to be done for one eye. The technique is able to cope with blinking, head movements, dim light, glasses and contact lenses.

Regarding the use of artificial neural networks (ANNs) for computation, this is of the more recently developed techniques. The raw material for eye-gaze tracking is still a digitized video image of the user, but this technique is based on a more wide-angled image of the user, so that the entire head is in the field of view of the camera. A stationary light is placed in front of the user, and the system starts by finding the right eye of the user by searching the video image for the reflection of this light—the glint, distinguished by being a small, very bright point surrounded by a darker region. It then extracts a smaller, rectangular part of the video image (typically only 40 by 15 pixels) centered at the glint, and feeds this to an ANN. The output of the ANN is a set of display coordinates. The ANN requires more than the simple calibration that is required by the other techniques; it must be trained by gathering images of the user's eye and head for at least three minutes while the user visually tracks a moving cursor on the display. This is followed by an automatic training session that uses the stored images lasting approximately 30 minutes using the current technology, but then the system should not require re-calibration on the next encounter. To improve the accuracy of an ANN-based system, the corneal/pupil based calculations can be augmented with a calculation based on the position of the glint in the eye socket. The great advantage of ANN-based techniques is that due to the wide angle of the base image, user head mobility is increased.

The eye tracking used in embodiments of the present invention can have many applications. For example, more than 9,000 paralyzed people operate computers and wheelchairs using eye trackers (most survivors of spinal injuries and neuromuscular diseases retain control of their eyes). Special software enables a person to type, and may include word-completion technology to speed up the process. Thousands of paralyzed people operate computers and wheelchairs using eye trackers. It is useful for these individuals because most survivors of spinal injuries and neuromuscular diseases retain control of their eyes. The technology can also be used to alert drowsy drivers, diagnose brain trauma, train machine operators and provide surgeons with "a third hand" to control robotic equipment. It can be used to remotely control a television. Eye tracking can be used in conjunction with desktop computers, video-games consoles and e-readers. For example, a tablet computer can be controlled using eye movements. Moving an on-screen cursor with a glance is much faster than using a mouse. Eye tracking can be done using inexpensive night-vision cameras.

Eye tracking can also keep an eye on drivers. In America each year more than 750 people are killed in road accidents involving drivers who fall sleep. One way to detect and alert a dozing driver is to use an ear clip that beeps when it detects the driver's head nodding forward. Eye tracking can be used in an attention monitoring system that sounds a warning if an eyelid sags, blinking speed slows, the shifting of the driver's gaze becomes sluggish or his head tips forward.

Eye tracking can also be used with scuba masks that detect fatigue, levels of blood oxygen and nitrogen narcosis, a form of inebriation often experienced on deep dives. Software can be incorporated that determines whether circular or radial muscles in the iris are opening or closing the pupil. Radial muscles take over as stress and brain effort increase. Because a novice's brain has to work harder than an expert's to perform a given task, this offers a way to measure a person's level of expertise.

Eye tracking also has military applications too. Eye tracking can be used to monitor the eye movements of pilots in flight simulators. The equipment can reveal whether trainees are scanning gauges in the right sequence, or skipping one altogether. Eye tracking can also have uses in real aircraft. In particular, it could be used to aim weapons just by looking at a target. At the moment a pilot aims by turning and tilting his head, the orientation of which is determined using helmet-mounted sensors. Eye tracking can be used for wirelessly controlling a drone.

More specifically, eye tracking can be used for Auto GCAS and Anti GLOC. Two subsystems that a spatial disorientation system can integrate are the Auto Ground Collision Avoidance System (A-GCAS) and the Anti G Induced Loss of Consciousness system (A-GLOC). If the eye tracker detects eye closure of a predefined extended duration or had detected nystagmus for an extended period, the pilot will be warned of the detection and the eminent seizure of control of the vehicle and provided with an opportunity to override vehicle control. If the user does not override, then the A-GCAS or A-GLOC systems will take control of the aircraft typically returning the vehicle to a safe attitude and possible directing the vehicle toward a home location.

In one embodiment of the SD/MS system integrated with other avionics systems, the SD/MS system monitors the flight conditions such as direction and change in direction, speed, vibration, flight time, visibility etc. This information is processed and indexed to a level of how provocative the environment is and has been to causing SD/MS. If the environment passes a threshold the SD/MS display symbology may be activated or enhanced depending on the level of provocation. These thresholds may be user specific. In further embodiments the system can be configured differently for different users based on their predetermined tolerance level.

Virtual Control Interface. In this use the optical tracker analyzes eye movements for a special use algorithm and provides flight/operator control inputs to the vehicular system and/or fire control inputs to a combat or law enforcement system.

Gaming Interface. In this use the optical tracker analyzes eye movements for a special use algorithm and provides gaming control inputs to the game controller and/or provide SD/MS display if the associated eye movements dictated its display.

4. Analysis of Eye Movement, Eye Closure and Abnormalities

As previously noted, embodiments of the present invention can use a camera to detect eye movement, eye closure (e.g. palpebrae closure), eyelid position detection and other eye parameters as described in the paragraphs that follow, and comprises eye activity such as nystagmus, saccades, blinking, eye muscle movement, eye closure rate, eye closure duration, palpebral position, frequency of eye closure, and velocity of eye closure. The eye sensor can measure the data in either one eye or both eyes. Embodiments of the present invention can then use this information to detect and respond to abnormalities.

A typical person makes 3-5 eye movements per second, and these movements are crucial in helping us deal with the vast amounts of information we encounter in our everyday lives. Spontaneous eye blinking serves a critical physiological function, but it also interrupts incoming visual information. This tradeoff suggests that the inhibition of eye blinks might constitute an adaptive reaction to minimize the loss of visual information, particularly information that a viewer perceives to be important. From the standpoint of physiology, blinks exist primarily to protect: They keep the eyes hydrated and protect against foreign objects. When the blinking process starts, the eye moves around 2° in the inferior nasal-ward direction while it performs a cyclo-torsional rotation. Simultaneously with these movements, the eye performs a retraction inside the orbit of 0.5-1.5 mm. The physiological function of these movements is still not clear. It is probable that eye retraction during blinking prevents excessive pressure of the eyelid over the cornea.

Average individual rates of blinking increase with age and are correlated with dopamine levels in human and nonhuman primates. However, blinking also relates, like other autonomic processes (e.g., heart rate, perspiration), to cognitive states beyond physiological function alone. Blink rate has been observed to vary as a function of several cognitive tasks, and blink rates decrease during activities that require greater attention, as when reading vs. sitting in a waiting room. Studies have also shown that the timing of blinks is related to both explicit and implicit attentional pauses in task content. Together, these observations highlight a key difference between blinking and other autonomic reactions.

Blinking sets a physical limit on visual attention because of its profound interruption of incoming visual information. Generally, humans blink at least about 5-30 times per minute or about 7,000-43,000 times per day. The typical duration of palpebrae closure is also variable during blinks, lasting 40 to 200-300 milliseconds. Each involuntary-reflexive blink generally averages about 250 milliseconds. This amounts to about 1,750-10,800 seconds per day of eye closure due to involuntary blinking. As tiredness or sleepiness occurs, the eye blinks may get longer and slower and/or the blink rate may vary, and/or the eyelids (e.g. palpebrae) may begin to droop with small amplitude eye lid blinks, e.g., until the eyes begin to close for short term "microsleeps," (i.e., sleep conditions that last for about 3-5 seconds or longer, or for prolonged sleep). Many other factors affect the duration of palpebral closure, such as drugs, alcohol, and medical conditions. Even individuals who have dry eyes can have a longer eyeblink duration. People with dry eyes can have a median extended blink duration of more than 2 times longer than that of normal.

Eye blinks are typically classified into three categories: spontaneous eye blinks (which occur frequently); reflexive eye blinks which are evoked by an external stimulus; and voluntary eye blinks, caused by intentional eye closing. Embodiments of the present invention can be used to identify and analyze these three types of blinks to discriminate between normal blinks and those associated with a condition indicative of spatial disorientation, drowsiness, or other kinds of performance impairment for the operator of a vehicle or the user of powered equipment.

Ocular indices related to eye blinks can include blink rate, blink duration, blink amplitude, percentage of eyelid closure, eyelid closing/opening speed or ratios of these indices. These ocular indices have the potential to be recorded by monitors that can warn drivers if they approach a sleepiness threshold. One advantage of ocular indices is that they can be recorded via non-contact methods such as video or infrared reflectance oculography. These non-contact recording methods are an advantage as drivers will not have to be concerned about correctly applying a sensor or sensors when using the monitor. One ocular index that has been shown to be effective as a measure of sleepiness is blink rate. Increased rate of blinking has been associated with increases in sleepiness. For instance, examinations of sleep-deprived individuals reveal positive correlations between blink rate and the amount of time spent awake. Moreover, subjective sleepiness has been positively correlated with time spent awake. Blink rates have also been found to increase during a 40-minute daytime vigilance task. Increases in blinking rates have an association with increases in sleepiness. The duration of eyelid closure (i.e. blink duration) is also suggested to be a sensitive measure of sleepiness. Blink frequency and duration have been associated with the performance of other attentional tasks (e.g., driving, piloting aircraft) and correlate with subjective sleepiness scales and electroencephalographic changes. Suppression or reduction of blinking occurs with tasks that have a high visual attention demand, such as reading. Blink duration correlates with increased sleepiness or fatigue and may provide a more significant index for alertness than blink frequency. Normal blink frequency is on the order of 9 to 13 per minute in the daytime, increasing to 20 to 30 per minute in sleep-deprived subjects or patients with abnormal sleep patterns. Regarding oculomotoric parameters, blink duration, delay of lid reopening, blink interval and standardized lid closure speed were identified as the best indicators of subjective as well as objective sleepiness. When tracking the eyelid activity, cameras that are placed too high and away from the user, tend to track poorly. Gaze lowering regularly occurs during driving simulation.

Saccades are quick, simultaneous movements of both eyes in the same direction controlled by the frontal lobe of the brain. Some irregular drifts, movements, smaller than a saccade and larger than a microsaccade, subtend up to six minutes of arc. Even when looking intently at a single spot, the eyes drift around. This ensures that individual photosensitive cells are continually stimulated in different degrees. Without changing input, these cells would otherwise stop generating output. Microsaccades move the eye no more than a total of 0.2° in adult humans. Covert corrective saccades (during head motion) and corrective overt saccades (post head motion) are strong indicators of a significant vestibular deficit.

Saccadic parameters and fixation durations also showed specific changes with increasing sleepiness. The spontaneous eye blink is considered to be a suitable ocular indicator for fatigue diagnostics. The reduction in average saccade velocity may be secondary to increases in blink frequency. Furthermore, the pupils may constrict more sluggishly, show unstable fluctuations in size, shrinking progressively in diameter, and/or demonstrate delayed responses to light flashes (i.e. delayed pupil response latency) as sleepiness and fatigue progresses. In addition, other ocular manifestations of (i.e., delayed saccadic response latency), with either over- or under-shooting the target, and/or a loss of directed gaze with or without binocular vergence or divergence, eye drift, or esophoria. Strabismus is another term that refers to a misalignment of the eyes. Esophoria refers to the deviation of the visual axis toward that of the other eye in the absence of visual fusional stimuli (e.g. the eyes tend to turn inward toward the nose). Exotropia refers to eyes that turn outward. It is the opposite of crossed eyes, or esotropia. This convergent strabismus can be related to drowsiness or alcohol ingestion. With alcohol ingestion one will also see reduced central visual acuity, reduced depth perception, spontaneous nystagmus on lateral gaze, increased corneal gloss, increased uniocular dominance and esophoria on distant vision and exophoria on near vision with concentrations in the range of 0.6 g/l-1.3 g/l. Some studies have suggested ocular functions are not affected until one reaches a threshold concentration of 0.7 g/l of alcohol.

External muscles control the movement of the eyeball and direct the eyes to a point of interest while keeping the retinal image in slight but constant motion. These extraocular muscles stabilize the eyes and must work together to keep both eyes centered on the point of interest. Four of these muscles control movement of the eye up, down, right and left. The remaining two muscles counteract the effects of head movement. The medial rectus muscle, also referred to as the internal rectus muscle, moves the eye inward toward the nose. This movement is called adduction. The lateral rectus muscle, sometimes called the external rectus muscle, turns the eye outward, away from the nose in abduction. Increased activity of this muscle will direct the eye laterally. The superior rectus muscle moves the eye upward, in a movement called elevation. It also rotates the top of the eye toward the nose in the movement of intorsion. It helps move the eye inward toward the nose. This muscle must work with the others to direct the eye straight up or down. The inferior rectus muscle turns the eye downward, in a movement called depression. As a secondary function, it helps turn the top of the eye away from the nose. The superior oblique muscle primarily rotates the top portion of the eye away from the nose in the extorsion movement. It also helps turn the eye upward. The inferior oblique muscle rotates the top of the eye away from the nose in extorsion. Secondarily, it moves the eye upward in elevation and helps turn the eye outward in abduction. Ciliary muscles adjust the shape of the lens to help the eyes focus. When the ciliary muscle contracts, the lens becomes rounder so the eyes can focus on close objects. When the muscles relax, the lens flattens and thins so the eyes can focus on distant objects. This movement of the ciliary muscles is called accommodation. The sphincter pupillae muscles are a group of smooth muscles that constrict the pupil to limit the amount of light that enters. If light levels increase, these muscles cause the iris to close, reducing pupil size. Conversely, the dilator pupillae muscles dilate the pupil and allow more light to enter when light levels are low. When light enters the pupil, it shines on light-sensitive cells in the retina and sends signals to the oculomotor nerve.

The eyelid (singularly called the palpebral and both eyelids are called palpebrae) refers to two folds of skin and muscle that can be closed over the exposed portion of the eyeball. The opening between the lids is called the palpebral aperture or palpebral fissure. The palpebral fissure is the elliptic space between the medial and lateral canthi of the two open eyelids (e.g. the longitudinal opening between the eyelids). In adults, this measures about 9-12 mm vertically. It is also referred as the height or distance of the palpebrae fissure (PF) between the upper and lower eyelid margins at the axis of the pupil. Normal measurement is 9 to 12 mm. The dimensions of the palpebral opening increase nearly 50% in width and 20% in height between infancy and adulthood. Configuration varies with a person's physical and racial characteristics. Ptosis is a lowering of the eyelid to below its normal position. It is an abbreviation of 'blepharoptosis' (a fallen eyelid) but this longer version is now almost never used. The degree of ptosis can be quantified clinically by measuring the vertical length of the palpebral fissure-about 9 mm in normal subjects, assuming the lower eyelid is normally positioned. A more useful measure is the distance between the upper lid margin and the mid-corneal reflex when the globe is in primary position. This is called the upper MRD. Upper marginal reflex distance (MRD) is the distance between the central corneal light reflex and upper eyelid margin with eyes in primary position. The severity of ptosis is better determined with upper MRD than PF measurements as lower lid malpositions are eliminated. Normal MRD is 4-5 mm. Ptosis can be defined as an upper MRD less than 2 mm or an asymmetry of more than 2 mm between eyes.

The distance between the corneal light reflex and the upper eyelid margin is termed the upper marginal reflex distance. Multiple muscles control the reflexes of blinking. The main muscles in the upper eyelid, which controls the opening and closing are the orbicularis oculi and levator palpebrae superioris (LPS) muscle and minor contribution from Muller's muscle. There are three types of blinks: one voluntary and two involuntary. Voluntary blinks occur with a conscious decision to momentarily close the eyes. One type of involuntary blink is considered to be protective, is produced in response to some potentially harmful stimulus, and is called as a blink reflex. A second type of involuntary blink occurs spontaneously about 15,000 times per day and keeps the cornea healthy by enabling a layer of moisture to form continuously. The blink of drowsiness has variable frequency and duration. It is highly related to the alertness states of the individual and therefore can detect drowsiness, Long blink refers to a blink that has duration longer than 500 ms. When the individual's alertness level decreases, the more long duration blink appears, and these blinks have long duration and low velocity. Therefore, the amplitude of blink will be lower than normal, and the average amplitude will decrease with more and more such blink appears.

The levator palpebrae superioris (LPS) is the primary muscle responsible for palpebral movement or lid elevation. It arises from the back of the orbit and extends forwards over the cone of eye muscles. It inserts a fibrous semicircular structure into the eyelid and the tarsal plate, which gives the upper eyelid its shape. The LPS is supplied by the superior division of the oculomotor nerve. The way that the LPS attaches to the tarsal plate is modified by the underlying Müller's muscle. This involuntary muscle, comprising sympathetically innervated smooth muscle, has the capacity to 'tighten' the attachment and so raise the lid a few millimeters. Two other muscles affecting the final position of the eyelid are the frontalis muscle and the orbicularis oculi, both supplied by the facial nerve. Frontalis contraction helps to elevate the lid by acting indirectly on the surrounding soft tissues, while orbicularis oculi contraction depresses the eyelid. The eyelid is held open when awake by the tonic action of LPS, punctuated intermittently by blinks. The upper eyelid normally covers the top 20% of the cornea but its exact position is determined by several factors. It rises and falls with vertical eye movements but it is also affected by the horizontal position of the eye, being slightly lowered when the eye is either adducted or abducted. The state of arousal influences lid position: fatigue is associated with reduced LPS activity but the overall level of sympathetic activity affects the tone in Müller's muscle so the eyelid sits slightly higher in circumstances associated with increased arousal.

height, palpebral aperture, marginal reflex distance, frequency of palpebral closure, velocity of palpebral closure, abnormal eye responses, prolonged eye closures or abnormal eye reflexes can be used as input of a controller of other operational firmware/software programs to control hardware in machine or other physical equipment involved in performing function in industry environments. This specifically would relate to controlling equipment if the user of the device employing embodiments of the present invention had abnormal eye responses. Measured abnormal eye recording could be used by the device that includes a software program that uses an algorithm to control the operation of the hardware. This device could be used in vehicular, medical, sporting, military, aerospace or any other commercial applications where human performance has importance in the operation of equipment. Embodiments of this invention can use normal or abnormal eye movement as a controller. As noted previously, any one of the measured eye movements such as the various types of nystagmus, abnormal twitching, jittering eye movements, abnormal eye blinks, prolonged eye twitching, prolonged eye twitching, saccadic eye movements, and prolonged eye closure could function as input to a controller.

The saccadic system controls fast eye movements to a target, and the smooth pursuit system controls eye movements to track a slowly moving target. During a re-direction gaze between near and far distances, the vergence system controls bilateral eye movements to bring a visual target of interest in focus. The fixation system acts to continually maintain eye position on a visual target, and the labyrinthine ocular reflex and optokinetic systems use appropriate and compensatory eye movements to maintain fixation during brief and sustained head movements, respectively. A rudimentary overview of the major neuronal structures involved in each system is provided in the table below. There is considerable overlap among the structures that make up each system.

| Structure | Fixation | VOR | OPK | Saccades | Smooth pursuits | Vergence (incompletely) |
|---|---|---|---|---|---|---|
| Brainstem | x | x | x | x | x | x |
| Cerebral cortex | x | | | x | x | x |
| Cerebellum | | x | | x | x | x |
| Basal ganglia | x | | | | x | ? |
| Superior colliculus | x | | | | | |
| Vestibular sensors (semicircular canals, otoliths) | | x | | | | |

The range of eyelid or palpebral movement from full elevation to closure ('eyelid excursion') is usually greater than 10 mm. This range can easily be measured. It forms an important part of the assessment of any individual with ptosis. Fatigability is assessed by detecting any lowering of the eyelid during sustained upgaze for at least 60 seconds. Ptosis (or lowering of the upper palpebral position) is present when the upper eyelid is less than 2 mm from mid-pupil. Reduction of the upper field of vision to 30 degrees or less is present in 97% of eyes with ptosis so defined. As noted, the normal vertical height of palpebral fissure is near 10 mm in adults. In drooping the vertical height would decrease and subtracting this from the normal height in the other eye would give the degree or the amount of the drooping. (Mild ptosis: 2 mm, Moderate ptosis: 3 mm, Severe ptosis: 4 mm).

Any measured abnormal eye movements, or abnormal palpebral movements, such as the palpebral position, palpebral closure rate, palpebral closure duration, palpebral fissure Characteristics of saccades that can be evaluated and assessed for pathologic changes include accuracy, latency (or initiation), amplitude (or angular distance traveled), and velocity (or amplitude per unit of time). Characteristics of saccades that can be evaluated and assessed for pathologic changes include accuracy, latency (or initiation), amplitude (or angular distance traveled), and velocity (or amplitude per unit of time).

As with saccades, pursuit characteristics include latency and velocity. Gain is a very important pursuit feature defined by the ratio of eye velocity to target velocity.

Characteristics of vergence eye movements include velocity, latency, and waveform or trajectory. Waveform is the pattern of velocity change during a vergence movement Fixation is an active process that holds the eyes steady on the target. In addition, eye movements occur during normal fixations that are imperceptible to the human eye. These are microsaccades (very small amplitude saccades), microdrifts (smooth, meandering eye movements of a very slow velocity), and microtremor (rapid oscillations with amplitudes much smaller than microsaccades). Other normal-fixation eye movements include square wave jerks, which are perceptible to the human eye. They consist of a saccade away from the visual target, followed by a saccade that returns the eyes to the visual target after a brief intersaccadic interval. A frequency of four to six square wave jerks per minute is normal, and a rate greater than 15 per minute is considered abnormal. Inappropriate disruptions or dysfunction within the pathways that make up the fixation eye movement system may result in nystagmus (sustained oscillations with two phases that either are both slow or have a slow and a fast phase), intermittent saccadic oscillations or saccadic intrusions, and sustained saccadic oscillations.

Optokinetic eye movements hold the visual target on fixation during sustained head rotation. Evaluation of induced optokinetic nystagmus (OKN) can be used to assess the functional status of optokinetic eye movements. OKN consists of a slow eye movement phase followed by a quick eye movement phase in the opposite direction. It is induced when a person is in constant motion and viewing stationary visual targets (the type of eye movements a passenger on a train might have while looking out the window at the scenery passing by).

A tracking system can manage the vergence, version, and tilt control with a stereo pair of cameras to fixate a target object. The separate controls allow a person to move the gaze toward the point of interest and to control the vergence angle to fixate the target. The main contribution of this work is the implementation of a sensor for an active vision system with dynamic vergence control to explore dynamic environments using a scheme different to the common static camera configurations. The main problem of an active system is that the rectification process is required each time that the camera configuration is modified. Therefore, the use of a static rectification preprocessing stage technique is unsuitable for any active system that actively modifies the vergence angle of its camera setups.

Even tracking eye movements that occur with head movements (e.g. the labyrinthine-ocular reflex) can be very helpful in sports and other activities. Recent studies showed significant differences for head and eye-head stabilization during the hitting sequence among professional tennis players. In brief, these studies suggested that gaze patters of elite tennis players have a specific fixation stage and that head and eyes stabilization on the contact zone has a strong influence on the success of hitting. In addition, these studies suggested a close relationship between head/eye stabilization at and after contact and the level of skill expertise.

Nystagmus is an involuntary oscillation of one or both eyes about one or more axes. Nystagmus is a term to describe fast, uncontrollable movements of the eyes that may be: side-to-side (horizontal nystagmus); up and down (vertical nystagmus), rotary (rotary or torsional nystagmus). Generally, the eyes move rapidly in one direction (fast phase or fast component) and slowly in another direction (slow phase or slow component). Depending on the cause, these movements may be in both eyes or in just one eye. The term dancing eyes has been used to describe nystagmus. The eyes of an individual with nystagmus cannot remain still and oscillate in some position of gaze. People experiencing nystagmus usually have decreased vision and poor depth perception, although those born with nystagmus may not realize that their vision is poor. Those with acquired nystagmus may experience double vision or oscillopsia, or that objects in their visual space appear to move. An acquired nystagmus may be accompanied by other symptoms such dizziness, difficulty with balance, hearing loss, poor coordination, and numbness. If an individual with nystagmus experiences oscillopsia, then the nystagmus is acquired. Broadly, nystagmus may be divided into one of three categories. (1) It may be induced physiologically as a result of some provoked stimulus (e.g. optokinetic, vestibular and end-point). 2) It can be present at birth or soon after, when it is referred to as congenital or infantile nystagmus. (3) It may be acquired (e.g. due to neurological disease, drug toxicity or other disorders). In health, nystagmus occurs during self-rotation in order to hold images of the visual world steady on the retina and maintain clear vision. Two forms of nystagmus are induced by self-rotation: optokinetic and vestibular. An optokinetic nystagmus is an involuntary, conjugate, jerk nystagmus that is seen when a person gazes into a large moving field. The oscillations, which are in the plane of the moving field, are generally 3-4° in amplitude and 2-3 Hz in frequency. Both cortical and subcortical pathways contribute to the response, which is driven by the retinal image slip velocity. Smooth pursuit inputs are of particular importance.

Vestibular nystagmus occurs during self-rotation. The inner ear contains motion detectors (vestibular labyrinth) that project to the vestibular nuclei and cerebellum. A vestibular nystagmus can also be induced by irrigating the ears with warm or cold water. With unilateral irrigation, the conjugate nystagmus is horizontal, vertical, torsional or oblique, depending on the position of the head. Both a convection mechanism and a direct temperature effect on the canal's sensory apparatus have been proposed to account for the involuntary oscillations.

Nystagmus is characterized by the degree of conjugacy, the plane or planes of the oscillation, the direction or directions of gaze, at which it is present, and the waveform (its amplitude and its frequency). Although a reasonable indication of the oculomotor behavior may be obtained by just viewing the eyes, greater clarity and precision is gained when oculographic techniques are used. When the eyes oscillate like a sine wave, it is called pendular nystagmus. If the nystagmus consists of drifts in one direction with corrective fast phases, it is called jerk nystagmus. Nystagmus is an involuntary rhythmic shaking or wobbling of the eyes. The term nystagmus is derived from the Greek word, "nmstagmos", which was used to describe the wobbly head movements of a sleepy or inebriated individual. Nystagmus has also been described as "dancing eyes" or "jerking eyes". Doctors and researchers classify nystagmus by the characteristics of the eye movements like do they move back and forth like a pendulum or do they move slowly in one direction and then rapidly in another.

There are over 45 types of nystagmus. Early onset nystagmus often accompanies vision loss acquired at birth or soon after and may be one of the first signs that a child has a loss of vision. Studies suggest 1 in every 1000 children have nystagmus. In 80-90% of cases, it is a side effect of vision loss from eye diseases such as albinism, aniridia, optic nerve hypoplasia, achromatopsia congenital cataracts, coloboma or retinopathy of prematurity. This type of nystagmus is usually observed around the sixth to eighth week of life and is rarely seen before then. In about 10-20% of cases, it presents with mild vision loss not associated with other diagnosed ocular diseases. The typical nystagmus related to vision loss during childhood is a pendular nystagmus. The eyes rotate back and forth evenly, much like a pendulum. Patients with early onset nystagmus do not notice the movement of their vision when their eyes shake. Although nystagmus is associated with early vision loss, it may vary from stress, emotional status and direction of view. It is uncommon to permanently worsen over time. In fact, nystagmus often improves mildly from childhood to adulthood. Most cases of early onset nystagmus are associated with ocular disease many of which are inherited conditions. Genetic counseling can help the patient and family understand the odds of passing the condition to their children. Not all cases of early onset nystagmus are hereditary. While vision loss before birth will result in nystagmus, loss of vision occurring later in life does not usually cause nystagmus.

Nystagmus can be acquired later in life due to neurological dysfunction such as a head injury, multiple sclerosis or brain tumors. Unlike nystagmus acquired from early in life, patients with late onset nystagmus usually notice movement in their vision related to the movement of their eyes. This is called oscillopsia. Oscillopsia causes a person to have vertigo or dizziness related to the new movement they experience in their vision. Late onset nystagmus is more likely to be directional. The eye will move slowly in one direction, then quickly move back. The nystagmus may change as the patient looks in different directions. The unexplained onset of nystagmus in an adult may indicate a serious neurological disorder and an immediate examination is indicated.

Some medications may cause nystagmus. For example, Dilantin and Phenobarbital, medications given to prevent seizures, may cause nystagmus. This acquired condition may cause the patient to experience oscillopsia, a sensation of movement in their vision that causes a vertigo effect. When it occurs vertically, the patient may describe a rolling of the vision in front of them.

Nystagmus patients often experience fluctuations in their vision. A change in the speed of the nystagmus leading to a decrease in vision can be related to stress, the patient's emotional state, fatigue, the direction of view or when one eye is covered. Understanding these issues allows the patient and teachers to create a better environment.

Patients with nystagmus often find a unique position of their head and eyes that slows the nystagmus allowing them to have better vision. This is called a null position and varies with each person.

Patients with nystagmus may report problems with balance. Impairment to binocular vision is common with early onset nystagmus and depth perception is indirectly impaired in many patients. Nystagmus acquired later in life may cause vertigo or dizziness like effects from the sensation of motion in the vision. Nystagmus may decrease when the eyes converge to read. Low vision specialists can add prism to induce convergence artificially and thus reduce the nystagmus in some patients.

Apparent motion was investigated as a stimulus for optokinetic nystagmus (OKN) and self-motion perception (vection). Apparent motion was stimulated by stroboscopically illuminating vertical stripes on the interior of a large drum that rotated about the observer at 20, 40 and 60 deg/sec. Pursuit occurred for all of these stimuli. However, OKN, OKAN and vection only occurred for frequencies equal to or greater than the threshold for continuous apparent motion. Our results suggest that pursuit can occur as a response to apparent motion generated by both small and large image displacements, while OKN and vection are responses to apparent motion generated by small image displacements only. These results suggest that different afferent sources are utilized for the control of pursuit and of the slow phase of OKN.

Spontaneous nystagmus denotes movement of the eyes without a cognitive, visual or vestibular stimulus. Most commonly spontaneous nystagmus is caused by a vestibular imbalance. Normally, both vestibular nerves fire at a tonic rate. The two nerves input are subtracted centrally. When the head is still, this will result in a signal of 0 spikes/second, and therefore no nystagmus will be present. When one vestibular nerve has decreased firing relative to the other, this provides an offset that produces a constant nystagmus. Vestibular nystagmus is "jerk" nystagmus"—the eye moves slowly towards the side of decreased firing, and then "jerks" back towards the center.

Vestibular nystagmus is typically inhibited by visual fixation. It also typically follows Alexander's law (it becomes greater upon gaze in direction of the fast phases). If the nystagmus does not follow these characteristics, it is likely not peripheral vestibular or there may also be other problems superimposed with the oculomotor system or central pathways. Processes that increase gaze-evoked nystagmus, such as ingestion of sedating medications, increase the effects of Alexander's law. In very high velocity vestibular nystagmus, or in persons with poor vision, fixation may be ineffective also.

Normal individuals are able to null out spontaneous nystagmus from minor fluctuations in vestibular tone over a period of days or weeks through a combination of low level automatic processes perhaps related to denervation hypersensitivity, and peripheral and central adaptation. This nulling out process is rapid, with the great majority being done in a few weeks. For complete unilateral lesions, a small residual nystagmus may persist for years. With this in mind, spontaneous nystagmus is abnormal, but its significance may not always be apparent. A spontaneous nystagmus today might be related to a recent, relatively minor vestibular imbalance or an ancient, complete unilateral vestibular loss. Spontaneous nystagmus must also be considered in the context of the recording method that one has available. Using highly sensitive recording methods such as video-ENG, or infrared, small amounts (e.g. 2 deg/sec) may be significant. Using the more common electronystagmogram recording, which is prone to drift, the upper limit of normal is 5 deg/second.

In Meniere's disease, vestibular imbalance type nystagmus is typically seen during an acute attack. Attacks typically last 2 hours only, but usually the next day or two there will be some nystagmus also. In about 85% of the cases, the nystagmus is horizontal with the fast component directed towards the healthy hearing ear, suggesting a vestibular paresis on the side to which the slow phases are directed. The nystagmus slow-phase velocity can reach as high as 40 deg/s. Occasionally nystagmus is also seen directed in the opposite direction. This may occur early on, reflecting a temporary excitation, or later, reflecting a recovery nystagmus (known as Bechterew's phenomenon).

Pendular nystagmus is caused by central lesions involving the central tegmental tract. The concept is that there is a feedback loop controlling eye position or velocity. Lesions add delays, causing instability and nystagmus. Multiple sclerosis is the most common cause of this sort of nystagmus. Dysmyelinating disorders such as Pelizaeus-Merzbacher is another example.

Sometimes a horizontal and vertical nystagmus will occur together. They are usually of the same frequency, but their relative phase may different. Depending on the mutual phase, the eyes may take on an oblique direction (form an ellipse). This seems possible however, as in a nystagmus called "windmill nystagmus", the vector of the horizontal nystagmus changes from right-left to up-down and back again, constantly.

Seesaw nystagmus is a rare binocular disorder characterized by alternating vertical skew deviation and conjugate ocular torsion. Jerk seesaw consists of torsional slow phases in one direction and quick phases in the opposite. In Pendular SSN, there are slow, smooth eye oscillations. Pendular SSN has frequently been found associated with visual disorders and may also be of congenital origin.

Dissociated Nystagmus is a nystagmus where oscillations are present only in one eye. It has been described in spasmus nutans, congenital nystagmus, and various brainstem disorders, as well as disorders where there has been monocular visual loss from an early age, or acquired later in life. The nystagmus is generally primarily vertical, has a pendular waveform, and is of low frequency with small amplitude.

Asymmetrical nystagmus can also be seen when the vergence system is involved in a nystagmus. For example, this can occur after a pontine hemorrhage.

Congenital nystagmus is a term that is applied a diverse group of abnormal eye movements that are noted at birth or shortly thereafter. Congenital nystagmus is included under the category of disorders of fixation because it can frequently present as a severe gaze-evoked nystagmus, and because it is often increased by attempts at fixation. Congenital nystagmus is universal in albinism and occurs in achromatopsia. Such patients usually show rounding of slow-phases, with convexity in the direction of gaze. Such "increasing exponential velocity profiles" are typical of congenital nystagmus. Several types of acquired nystagmus appear similar to congenital nystagmus. These have been discussed earlier in this disclosure. Nystagmus of the blind is a constantly present nystagmus that may undergo periodic changes in direction.

Upbeat nystagmus has been described in lesions of the medulla, the ventral tegmentum, the anterior vermis of the cerebellum, and the adjacent brachium conjunctivum and midbrain. Upbeat nystagmus also is found in smokers as a side effect of nicotine, and as a side effect of other medications. UBN has been reported in association with Wernicke's encephalopathy, multiple sclerosis, brainstem infarction and other lesions. Some forms of Up Beating Nystagmus were explained by disruption of the ventral tegmental pathway for the upward VOR (vestibulo-ocular reflex).

Down Beat Nystagmus is classically attributed to the Chiari malformation. Numerous large studies have been published. These studies largely conclude that while the Chiari may contribute as many as ⅓ of cases, cerebellar degenerations, demyelinating disease, drug toxicity, neoplasia, and "idiopathic" are other common causes.

Torsional nystagmus in primary position (the eyes centered, person sitting upright) is very rare. Torsional nystagmus is more commonly elicited by positional maneuvers such as the Dix-Hallpike test. In that context, torsional nystagmus is generally attributed to benign paroxysmal positional vertigo (BPPV). Torsion is movement of the eye about its visual axis (note that we do not define it as about the front-back axis of the head). The term "rotary nystagmus" is used interchangeably. Torsional nystagmus, not pendular but jerk, is commonly elicited by positional maneuvers such as the Dix-Hallpike test. In that context, the nystagmus is transient, and not continuous. Torsional nystagmus is generally attributed to benign paroxysmal positional vertigo (BPPV), but also occurs in Migraine, and occasionally in lesions of the cerebellar nodulus.

Torsional nystagmus also occurs (rarely) in superior canal dehiscence syndrome, when it may be pulse synchronous. This nystagmus is due to pulsations in spinal fluid pressure that directly affect the cupula of the superior semicircular canal. Torsional nystagmus in primary position (the eyes centered, person sitting upright) is very rare. In midbrain lesions, small amounts of torsional nystagmus may last for years. In midbrain lesions, vertical saccades are often slowed.

Seesaw nystagmus is a conjugate pendular torsional oscillation with a superimposed disjunctive vertical movement. The intorting eye rises and the opposite extorting eye falls. Most patients with seesaw nystagmus have bitemporal hemianopia consequent to large parasellar tumors expanding within the 3rd ventricle. Seesaw nystagmus is exceedingly rare.

Head-shaking nystagmus is the nystagmus evoked by moving the head sinusoidally, typically for approximately 20 cycles.

Hyperventilation induced nystagmus has been reported in patients with acoustic neuroma and other CP angle tumors, in microvascular compression, in perilymph fistula, and in patients with MS and patients with cerebellar dysfunction.

Under video Frenzel goggles, it is common to see nystagmus provoked by vibration over the ears, over the front or back of the neck. This nystagmus is presently under investigation by several groups. In persons with unilateral vestibular loss, a nystagmus occurs nearly 100% of the time on vibration over the SCM muscles, with slow-phases directed toward the side of lesion. While the slow-phase velocity may not be very high, the nystagmus can easily be seen as being different from normal fixation behavior. In many normal individuals nystagmus is produced that beats to the left on stimulation of the left side and to the right on the right side. This is not associated with any known pathology.

About 85% of positional nystagmus is due to BPPV. In the remainder, most are "idiopathic". A small number of people have an identifiable brainstem or cerebellar disorder. Many healthy individuals show a small-amplitude($<2°$ conjugate jerk nystagmus on far eccentric gaze)($>40°$. These oscillations are thought to reflect the time constant of the gaze-holding control system and in particular the cerebellar neural integrator.

Many forms of acquired nystagmus can be attributed to disturbances of the three mechanisms that normally ensure steady gaze-visual fixation, the vestibulo-ocular reflex, and the mechanism that makes it possible to hold the eyes at an eccentric eye position (e.g. far right gaze).

Diseases affecting the visual system, such as retinal disorders causing visual loss, commonly lead to nystagmus because visual fixation is no longer possible. Disease affecting the vestibular organ in the inner ear causes an imbalance that leads to a mixed horizontal-torsional nystagmus, usually associated with vertigo. Disease affecting the central connections of the vestibular system, including the cerebellum, may cause several forms of nystagmus. These include downbeat, torsional, periodic alternating and seesaw nystagmus. None of these nystagmus types are, in themselves, pathognomonic of central nervous system disease. Downbeat nystagmus is usually associated with lesions of the vestibulo-cerebellum (flocculus, paraflocculus, nodulus and uvula) and the underlying medulla. Upbeat nystagmus is most commonly reported with lesions of the medulla, including the perihypoglossal nuclei and adjacent vestibular nucleus (both structures are important for gaze-holding), the ventral tegmentum and the anterior vermis of the cerebellum. Periodic alternating nystagmus is often linked to cerebellar disease (note that in this case the horizontal jerk nystagmus spontaneously reverses direction of the quick phase every few seconds). Seesaw nystagmus is linked to parasellar lesions of the optic chiasm (e.g. pituitary tumors) and achiasma. Note that seesaw nystagmus is a rare form of pendular nystagmus in which the torsional components are conjugate and the vertical components are disjunctive-one eye rises and intorts while the other falls and extorts. Gaze-evoked nystagmus is commonly seen as a side-effect of drugs, including sedatives, anticonvulsants and alcohol, as well as cerebellar disease.

Lesions affecting the medial longitudinal fasciculus cause internuclear ophthalmoplegia. A unilateral internuclear ophthalmoplegia is commonly related to ischemia, whilst bilateral internuclear ophthalmoplegias are associated with multiple sclerosis. An adduction weakness on conjugate movements and a jerk nystagmus of the abducting eye are the classic ocular motor signs ('dissociated nystagmus').

An acquired pendular nystagmus can occur in any plane; it can be monocular or have a greater intensity in one eye and typically remains pendular in all directions of gaze. It is associated with a wide range of brainstem and cerebellar disease including several disorders of myelin and with drug toxicities.

One of the most studied and frequently seen of the acquired oscillations is gaze-evoked nystagmus. The nystagmus is elicited when the patient attempts to maintain an eccentric eye position. Gaze-evoked nystagmus is the nystagmus that is provoked by particular directions of gaze. It is seen in patients with cerebellar disease (particularly the flocculus), muscle palsy and drug toxicity. A failure of the step (or tonic) eye position command from the gaze-holding network (the neural integrator) is deemed the reason for the presence of the nystagmus. After the eyes are returned to the primary position, a short-lived reflex nystagmus with quick phases opposite to the direction of the previous eccentric gaze oscillation can typically be seen in vestibulocerebellar diseases.

Diseases affecting the vestibular labyrinth or nerve (including the root entry zone) cause a jerk nystagmus with linear or constant velocity slow phase drifts. Characteristically the nystagmus increases when the eyes are turned in the direction of the quick phases (Alexander's law), and can be markedly suppressed by visual fixation. The direction of the unidirectional nystagmus is related to the geometrical relationship of the semicircular canals with the fast phase opposite to the side of the lesion. A change in head position often exacerbates the nystagmus. On the other hand, a central vestibular nystagmus, which is caused by disease of the brainstem and/or cerebellum, is not attenuated by fixation and invariably exhibits bidirectionality to the nystagmus (i.e. left-beating on left gaze and right-beating on right gaze).

The most common cause of acquired nystagmus is certain drugs or medication. Phenytoin (Dilantin)—an anti-seizure medication, excessive alcohol, or any sedating medicine can impair the labyrinth's function. Other causes include head injury from motor vehicle accidents, inner ear disorders such as labyrinthitis or Meniere's disease, stroke, and thiamine or vitamin B12 deficiency. Any disease of the brain, such as multiple sclerosis or brain tumors, can cause nystagmus if the areas controlling eye movements are damaged.

Approximately 60% of healthy human subjects experience motion sickness when exposed to a rotating optokinetic drum. Vection data (illusory self-motion), horizontal eye movement recordings, subjective motion sickness report, and a measure of gastric myoelectric activity (electrogastrogram, EGG) were obtained from 45 subjects. The results showed that fixation greatly reduced nystagmus and slightly reduced vection. The restricted visual field slightly reduced nystagmus and greatly reduced vection. Both of these manipulations significantly reduced symptoms of motion sickness and the self-perception of motion.

Both self-motion perception and presence can benefit from adding moving auditory stimuli. This has important implications for both multimodal cue integration theories and the applied challenge of building affordable yet effective motion simulators. Subjects seated in darkness often experience illusory self-rotation when exposed to a rotating sound field. Compelling illusions of self-rotation are generally accompanied by nystagmoid movements of the eyes with the slow phase in the direction opposite that of the experienced self-rotation. These phenomena are related to the functioning of a spatial constancy mechanism by which a stable distinction is normally maintained between movements of self and movements of the environment. The appearance of nystagmus during illusory self-rotation indicates that apparent body orientation can influence oculomotor control.

Ordinarily, eye movements prevent slip of images upon the retina from exceeding about 4 degrees per second. If retinal image velocity (RIV), commonly called, "retinal slip," exceeds 4 degrees per second, then visual acuity begins to decline and oscillopsia (an illusory movement of the stationary world) may result. Pursuit eye movements allow primates to follow moving objects with the eyes. When a target of interest starts to move, after a latency period of 120 ms, the eye accelerates smoothly in the direction of target motion to reduce the error between eye velocity and target velocity, i.e., retinal slip. Eye acceleration increases with the retinal slip and saturates at a value between 200 and 400°/s2 for non-periodic tracking in primates. In the middle of this acceleration period, a "catch-up" saccade is generated to reduce the error between eye and target positions that accumulated during the latency period. The catch-up saccade brings the image of the target on the region of the retina where visual acuity is the highest, the fovea. In primates, smooth pursuit gain, the ratio of eye velocity to target velocity, is close to unity. This indicates that at the end of the acceleration period, eye velocity almost perfectly matches target velocity. The period during which eye velocity matches target velocity is often referred to as steady-state pursuit. During steady-state pursuit in primates, eye velocity oscillates around a mean value. The frequency of this oscillation varies between 3.8 and 6 Hz and could reflect the delays inherent in the operation of a visual feedback loop. Retinal image slip promoted by fixational eye movements prevents image fading in central vision. However, in the periphery a higher amount of movement is necessary to prevent this fading. Even when the eye is fixating a point target it is not totally motionless because fixational eye movements keep it moving incessantly. There are three types of fixational eye movements: tremor, drift, and microsaccades. Tremor is an aperiodic, wave-like motion with velocities of approximately 20 minutes of arc/sec and amplitude smaller than the diameter of a foveal cone. Drift movements occur simultaneously with tremor, are larger and slower than tremor, with velocities in the order of 4 minutes of arc/second, and mean amplitudes of around 2-5 minutes of arc. This amplitude corresponds to a movement of the retinal image across a dozen photoreceptors. Fixational microsaccades, also called 'flicks' in early studies, are small and fast eye movements that occur during voluntary fixation. Typically, with peak velocities above 600 minutes of arc/sec, their amplitude ranges from 1 to 120 minutes of arc and they carry the retinal image across a width corresponding to several dozen to several hundred photoreceptors.

The occurrence of systematic inter-ocular differences in the time of initiation of saccades in various directions has been noted. In the initial phase of horizontal saccades, the nasalward moving eye lags the temporalward moving eye consistently by slightly less than 1 ms. No difference is found in vertical (upward or downward) saccades. In oblique saccades, the systematic initial lag of the nasalward moving eye is similarly present in the horizontal component of the saccade, but absent in the vertical component. It is suspected that this inter-ocular timing difference in horizontal saccades is due to the additional synaptic delay caused by the abducens internuclear neuron in the pathway to the medial rectus muscle of the eye. The final motor pathways, including the differences in the innervation of the medial and lateral rectus motor neurons, are identical for saccades and the vestibular ocular reflex, and in the absence of mechanical disturbances related to head movements the lag of the nasalward moving eye relative to the temporalward moving eye should be clear and consistent, once it is adequately looked for. On the other hand, such systematic timing differences should be absent in vertical saccades, for which the low-level motor circuits are symmetrical for the two eyes.

The 1 ms time lag in the initiation of the activity of the medial rectus muscle, compared to the contralateral lateral rectus muscle, should be sharply distinguished from the overall differences in the shape of the saccadic velocity profiles of the two eyes. The synaptic delay by itself can only account for the differences in the very first phase of the saccade, when the accelerations of the two eyes rise in parallel, with a virtually pure time-shift. Once the accelerations approach their first maximum, their peak values and further time courses are distinctly non-parallel in the two eyes. As a result, the peak velocities of the two eyes differ not only in magnitude but also in timing, by an interval that is substantially longer (on the order of 5 ms) than a single synaptic delay, with the abducting eye always having the advantage. These asymmetries, which are superimposed upon the difference in starting time, may be caused by differences in either muscular mechanics and/or in the innervation patterns, other than a simple lag.

The explanation of the timing difference in abduction and adduction on the basis of the low-level oculomotor pathways is further corroborated by the absence of any substantial or systematic inter-ocular difference in the timing or dynamics of vertical saccades. This agrees with the right-left symmetry of the vertical oculomotor pathways.

Impulse testing, which accurately measures the gain of the vestibular ocular reflex is mostly recorded from only one eye. Vestibular ocular reflex acceleration gains are similar for each eye in both directions at low accelerations, but as head acceleration increased, gains of the adducting eye exceeded gains of the abducting eye. These inter-ocular vestibular ocular reflex gain differences are due to longer latencies but higher accelerations of the adducting eye compared to the abducting eye. Consequently, directional vestibular ocular reflex gain asymmetry occurs at high accelerations if the same eye is always measured, with an average inter-ocular difference of 15.3%. If only the abducting eye is measured, vestibular ocular reflex gains appear symmetrical in both directions. For accurate measurements of the vestibular ocular reflex at high accelerations, the inter-ocular vestibular ocular reflex gain differences require binocular recording.

An object moving in depth produces retinal images that change in position over time by different amounts in the two eyes. This allows stereoscopic perception of motion in depth to be based on either one or both of two different visual signals: inter-ocular velocity differences and binocular disparity change over time. Disparity change over time can produce the perception of motion in depth. Inter-ocular velocity differences contribute to the perception of motion in depth and the human visual system contains mechanisms for detecting differences in velocity between the two eye's retinal images.

Despite this incessant retinal motion, images are perceived as static and clear. The visual system has mechanisms to deal with movement and the eventual blur resultant from the retinal image slip caused by fixational eye movements. These mechanisms fail when the amount of movement is above their capacity of neutralization. In these conditions, the image is perceived as blurred due to motion smear. An immediate consequence of blur is a diminution of resolution. Gaze control in various conditions is important, since retinal slip deteriorates the perception of 3-D shape of visual stimuli. Several studies have shown that visual perception of 3-D shape is better for actively moving observers than for passive observers watching a moving object. When a stationary viewer is watching compelling moving scene, he or she can report sensation of self-motion illusion (called vection).

Vection has been found to be correlated with levels of visual induced motion sickness (VIMS) and postural status. The correlation between vection and VIMS is consistent with the sensory conflict theory because sickness is generated in a sensory conflict situation where a person is reporting illusion of self-motion while remain physically stationary. The correlation between vection and VIMS has led to the term "vection induced motion sickness". One theory linking VIMS with inappropriate eye movements is consistent with the findings that suppression of eye movements by fixation can significantly reduce levels of VIMS. It has been hypothesized that the afferent signals in the ocular muscles will trigger vagal nuclei, resulting in a range of sickness symptoms associated with the autonomous nervous systems—the nystagmus theory. Because eye movements follow foveal stimulation and vection follows peripheral stimulation, the nystagmus theory indicates that in the presence of foveal stimulation, sickness will correlate with eye movements but not necessarily with vection. Since then, there have been competing studies reporting the decoupling between vection and VIMS as well as coupling between vection and VIMS. Some have felt that vection and motion sickness can be distinct phenomena and have further described Optokinetic stimulation generating circular-vection, and vection generated during a simulation of forward motion in a car as linear vection. In a prior study using an Optokinetic drum with this technology it was seen that both vection scores and simulator sickness scores were statistically significantly lower than when the technology was not used. Circular vection refers to the illusion of self-motion induced by rotating visual or auditory stimuli.

Visually induced vection can be quite compelling, and the illusion has been investigated extensively for over a century. Vection can be defined as a sensory-spatial illusion that creates false sensations of self-motion, in either linear or angular directions. Although false perceptions of self-motion are common, visual characteristics linked to this type of illusion are not fully understood. Vection can be strongly influenced by various physical aspects. Rotating auditory cues can also induce vection, but only in about 25-60% of blindfolded participants. Furthermore, auditory vection is much weaker and far less compelling than visual vection, which can be indistinguishable from real motion. Spatializing the fountain sound, such that it moved in accordance with the fountain in the visual scene, improves vection significantly in terms of convincingness, vection buildup time, and presence ratings. Most people know the phenomenon of vection from real-world experience. When sitting in a train waiting to depart from the train station and watching a train on the neighboring track pulling out of the station, one can have the strong impression of moving oneself, even though it was in fact the train on the adjacent track that just started to move. A similar effect can be observed when sitting in the car waiting for the traffic light to turn green and when a close-by large truck slowly starts to move.

In health, control mechanisms for maintaining steady gaze-fixation include: (a) the vestibulo-ocular reflex; and (b) a gaze-holding system (the neural integrator) that operates whenever the eyes are required to hold an eccentric gaze position. Failure of any of these control systems will bring about a disruption of steady fixation. Two types of abnormal fixation can result-nystagmus and saccadic intrusions/oscillations. The essential difference between them lies in the initial movement that takes the line of sight off the object of regard. In the case of nystagmus, it is a slow drift or 'slow phase' often due to a disturbance of one of the three mechanisms for gaze stability. On the other hand, with either saccadic intrusions or saccadic oscillations, an inappropriate fast movement moves the eyes off target.

5. Physiology-based Biometric Measurement

Physiology-based biometrics is not only concerned with identifying a person based on his/her physiological characteristics. It also includes the measuring of specific biological and physiological aspects of the individual. Previous examples of physical biometrics systems include fingerprint, hand, face, eye (iris or retina), and speech recognition. However many more physiology-based measurements can be identified from the individual and used to control powered equipment systems. Specifically by the identification of abnormal values of the physiology-based metrics, this data can then be the input for the controller action of the powered equipment. The premise is that specific abnormal physiology-based metrics represent factors that cause the operator to fail to properly operate vehicle or equipment safely. In embodiments of the present invention, the data received from the physiology-based sensors described in this disclosure and/or stored by the system can be used to detect abnormal values and initiate actions to properly control vehicles or powered equipment.

Skin sensors can be used in embodiments of the present invention to detect blood alcohol levels. The skin sensors can be touch-based and as such would require skin contact. The sensors could be incorporated into a vehicle. For example, they could be part of a steering wheel that can detect alcohol thru the pores of your skin. These sensors could also be placed anywhere on the skin, even on eyewear which contacts the skin. The amount of alcohol in the blood stream is referred to as Blood Alcohol Level (BAL). It is recorded in milligrams of alcohol per 100 milliliters of blood, or milligrams percent. The BAL of 0.10 means that $1/10$ of 1 percent (or $1/1000$) of the total blood content is alcohol. When a person drinks alcohol it goes directly from the stomach into the blood stream. This is why people typically feel the effects of alcohol quite quickly, especially if drinking on an empty stomach. BAL depends on the amount of blood (which increases with body weight), and the amount of alcohol consumed over time. Drinking fast will quickly raise a drinker's BAL because as the liver can only handle about a drink per hour—the rest builds up in your blood stream. A BAL of 0.08 is the legal limit for drunk driving in most states. With a BAL of 0.15, you experience impaired balance and are noticeably drunk. Many people lose consciousness with a BAL of 0.30 or higher, and breathing can stop with a BAL of 0.50, at which point many people die.

Embodiments of the present invention can use optical technology such as near-infrared absorption spectroscopy to measure blood alcohol content. The light enters the skin and a detector collects reflected light. This technique uses a helium-neon laser as the internal reference source, and is a non-invasive alternative to current methods. Spectrometry utilizes the near infrared region of the electromagnetic spectrum (from about 0.7 µm to 2.5 µm) to measure substances of interest in bodily tissue. The measurement begins when the biosensor touches the operator, which illuminates the operator's skin with NIR light, which propagates into the tissue. The beam of light can penetrate tissue at depths of up to 5 mm to reach the dermal layer where alcohol that is dissolved in water resides. A portion of the light is diffusely reflected back to the skin's surface and collected by an optical touch pad. The light contains information on the unique chemical information and tissue structure of the user. This light is analyzed to determine the alcohol concentration and, when applicable, verify the identity of the user. The data collected can then transmitted by blue tooth technology, in real time, to the vehicle or powered equipment the operator is operating. It can also be transmitted to a remote source. The powered equipment can then be programmed to shut down for safety reasons and the remote source can be notified of the blood alcohol levels.

Spectroscopy is a technique used to study the make-up of an object based on the light it emits. Each chemical element has a unique signature, emitting or absorbing radiation at specific wavelengths. For example, sodium, used in street lights, emits primarily orange light. Oxygen, used in neon lights, emits green light. By passing the light from a star or other object through a special instrument, called a spectrograph, the light is "spread" into a spectrum in much the same way visible light is spread into its colors by a prism. New types of physiologic biosensors can detect minute concentrations of blood glucose and it's an inherently non-invasive way to estimate blood glucose content in the body.

Embodiments of the present invention can use nanoscale biosensors. Hybridization of nanoscale metals and carbon nanotubes into composite nanomaterials has produced some of the best-performing biosensors to date. A scalable nanostructured biosensor based on multilayered graphene petal nanosheets (MGPNs), Pt nanoparticles, and a biorecognition element (glucose oxidase) would such an example for an embodiment of this invention. The combination of zero-dimensional nanoparticles on a two-dimensional support that is arrayed in the third dimension creates a biosensor platform with exceptional characteristics.

Embodiments of the present invention can detect respiratory acidosis. Respiratory acidosis is a condition in which a build-up of carbon dioxide in the blood produces a shift in the body's pH balance and causes the body's system to become more acidic. This condition is brought about by a problem either involving the lungs and respiratory system or signals from the brain that control breathing. Respiratory acidosis may be suspected based on symptoms. A blood sample to test for pH and arterial blood gases can be used to confirm the diagnosis. In this type of acidosis, the pH will be below 7.35. The pressure of carbon dioxide in the blood will be high, usually over 45 mmHg. Physiologic biosensors on the skin can detect the pH, oxygen saturation or percent (%) of oxygenation in the body. Abnormal levels will affect the performance of operators of powered equipment and physiologic biosensors can detect these abnormal values. As the abnormal levels are identified, they trigger the algorithm to properly control the powered equipment. With further technology advances, measuring and monitoring of vital signs and blood chemistry values will be evaluated with distally placed physiologic biosensors.

Embodiments of the present invention can detect blood pressure. The term hypertensive emergency is primarily used as a specific term for a hypertensive crisis with a diastolic blood pressure greater than or equal to 120 mmHg and/or systolic blood pressure greater than or equal to 180 mmHg. Hypertensive emergency differs from hypertensive crisis in that, in the former, there is evidence of acute organ damage. In physiology and medicine, hypotension is low blood pressure, especially in the arteries of the systemic circulation. Blood pressure is the force of blood pushing against the walls of the arteries as the heart pumps out blood. Hypotension is generally considered to be systolic blood pressure less than 90 millimeters of mercury (mm Hg) or diastolic less than 60 mm Hg.

Embodiments of the present invention can detect heart function. Bradycardia is the resting heart rate of under 60 beats per minute (BPM), although it is seldom symptomatic until the rate drops below 50 BPM. It sometimes results in fatigue, weakness, dizziness and at very low rates fainting. Bradycardia during sleep is considered normal and rates around 40-50 BPM are usual. A diagnosis of bradycardia in adults is based on a heart rate less than 60 BPM. This is determined usually either via palpation or an EKG. Tachycardia is a heart rate that exceeds the normal range. A resting heart rate over 100 beats per minute is generally accepted as tachycardia. Tachycardia can be caused by various factors that often are benign. However, tachycardia can be dangerous depending on the speed and type of rhythm. Note that if it is pathological, a tachycardia is more correctly defined as a tachyarrhythmia. The upper threshold of a normal human resting heart rate is based upon age. Tachycardia for different age groups is as listed below. An electrocardiogram (ECG) is used to classify the type of tachycardia. They may be classified into narrow and wide complex based on the QRS complex.

1-2 days: >(greater than) 159 beats per minute (BPM)
3-6 days: >166 BPM
1-3 weeks: >182 BPM
1-2 months: >179 BPM
3-5 months: >186 BPM
6-11 months: >169 BPM
1-2 years: >151 BPM
3-4 years: >137 BPM
5-7 years: >133 BPM
8-11 years: >130 BPM
12-15 years: >119 BPM
>15 years-adult: >100 BPM When the heart beats excessively or rapidly, the heart pumps less efficiently and provides less blood flow to the rest of the body, including the heart itself. The increased heart rate also leads to increased work and oxygen demand by the heart, which can lead to rate related ischemia.

Embodiments of the present invention can include physiological sensors that measure brain activity. Electroencephalography (EEG) is one of the methods used to record the electrical potential along the scalp produced by the neurons within the brain. Some waveforms in the EEG signal are highly correlated with the individual's sleepiness level. Electrical activity emanating from the brain is displayed in the form of brainwaves. There are four categories of these brainwaves, ranging from the most activity to the least activity: beta; alpha, theta and delta.

When the brain is aroused and actively engaged in mental activities, it generates beta waves. These beta waves are of relatively low amplitude, and are the fastest of the four different brainwaves. The frequency of beta waves ranges from 15 to 40 cycles a second. Beta waves are characteristics of a strongly engaged mind. A person in active conversation would be in beta. A debater would be in high beta. A person making a speech, or a teacher, or a talk show host would all be in beta when they are engaged in their work.

The next brainwave category in order of frequency is alpha. Where beta represented arousal, alpha represents non-arousal. Alpha brainwaves are slower and higher in amplitude. Their frequency ranges from 9 to 14 cycles per second. A person who has completed a task and sits down to rest is often in an alpha state. A person who takes time out to reflect or meditate is usually in an alpha state. A person who takes a break from a conference and walks in the garden is often in an alpha state.

The next state, theta brainwaves, are typically of even greater amplitude and slower frequency. This frequency range is normally between 5 and 8 cycles a second. A person who has taken time off from a task and begins to daydream is often in a theta brainwave state. A person who is driving on a freeway, and discovers that they can't recall the last five miles, is often in a theta state—induced by the process of freeway driving. The repetitious nature of that form of driving compared to a country road would differentiate a theta state and a beta state in order to perform the driving task safely. Individuals who do a lot of freeway driving often get good ideas during those periods when they are in theta. Individuals who run outdoors often are in the state of mental relaxation that is slower than alpha and when in theta, they are prone to a flow of ideas. This can also occur in the shower or tub or even while shaving or brushing your hair. It is a state where tasks become so automatic that you can mentally disengage from them. The ideation that can take place during the theta state is often free flow and occurs without censorship or guilt. It is typically a very positive mental state.

The final brainwave state is delta. Here the brainwaves are of the greatest amplitude and slowest frequency. They typically center on a range of 1.5 to 4 cycles per second. They never go down to zero because that would mean that you were brain dead. But, deep dreamless sleep would take you down to the lowest frequency—typically 2 to 3 cycles a second.

When we go to bed and read for a few minutes before attempting sleep, we are likely to be in low beta. When we put the book down, turn off the lights and close our eyes, our brainwaves will descend from beta, to alpha, to theta and finally, when we fall asleep, to delta. It is a known fact that humans dream in 90-minute cycles. When the delta brainwave frequencies increase into the frequency of theta brainwaves, active dreaming takes place and often becomes more experiential to the person. Typically, when this occurs there is rapid eye movement, which is characteristic of active dreaming. This is called REM, and is a well-known phenomenon.

When an individual awakes from a deep sleep in preparation for getting up, their brainwave frequencies will increase through the different specific stages of brainwave activity. That is, they will increase from delta to theta and then to alpha and finally, when the alarm goes off, into beta. If that individual hits the snooze alarm button they will drop in frequency to a non-aroused state, or even into theta, or sometimes fall back to sleep in delta. During this awakening cycle it is possible for individuals to stay in the theta state for an extended period of say, five to 15 minutes—which would allow them to have a free flow of ideas about yesterday's events or to contemplate the activities of the forthcoming day. This time can be an extremely productive and can be a period of very meaningful and creative mental activity.

In summary, there are four brainwave states that range from the high amplitude, low frequency delta to the low amplitude, high frequency beta. These brainwave states range from deep dreamless sleep to high arousal. The same four brainwave states are common to the human species. Men, women and children of all ages experience the same characteristic brainwaves. They are consistent across cultures and country boundaries.

Research has shown that although one brainwave state may predominate at any given time, depending on the activity level of the individual, the remaining three brain states are present in the mix of brainwaves at all times. In other words, while somebody is an aroused state and exhibiting a beta brainwave pattern, there also exists in that person's brain a component of alpha, theta and delta, even though these may be present only at the trace level.

Embodiments of the invention disclosed can include voice or specific voice commands. Embodiments can also include other abnormal physiology based biometric or physiology-based sensors and algorithms not mentioned in this disclosure that are capable of being understood by anyone skilled in the art.

For all physiologic biosensors, abnormal values detected can be used to trigger a control signal to a vehicle or powered equipment and this control signal can elicit a pre-programmed response. These abnormal values can also be sent via a wired or wireless protocol (such as WiFi, a cellphone signal, or by Blue Tooth technology), in real time, to a remote source to notify the remote location of the status of the operator. Additionally the operator can receive an alarm, which can be auditory, visual, or haptic. Even normal physiology-based biometrics including voice as "voice command controllers" can trigger the controller which can then, as with the abnormal eye movements, control the vehicle or powered equipment.

6. Further Application Areas for Embodiments of the Present Invention

Embodiments of the present invention can be used in any application where human performance is diminished and where abnormal eye movements, eye responses, eyelid activity or other physiological based biometrics can be monitored, measured, and used to control vehicular response or powered equipment. The reasoning is that the human response or lack of human performance can precede vehicular or powered equipment response. Specifically, human centric responses can precede vehicular or powered equipment responses. In any situation where human response or biometric responses are measured, detecting an abnormal physiological effect or biochemical response can help prevent an adverse response while operating a vehicle or powered equipment. If the operator has abnormal eye movements, abnormal eyelid movements or position, abnormal vital signs or other abnormal physiological based biometrics, which could impair the operator's ability to operate the equipment or vehicle, the physiologic biosensors of this disclosure can record the abnormal responses and send the data by way of an electronic interface to a controller system which can safely operate the vehicle or powered equipment. All of the data acquired (such as storage of the measured eyelid positions or eye movement can be stored in a computer-readable memory unit for later retrieval.

A variety of medical conditions can be monitored. Examples include petit mal epilepsy, in which the eyes flutter at a rate of about three cycles per second, grand mal or psychomotor seizures, where the eyes may stare or close repetitively in a jerky manner, myoclonic seizures, in which the lids may open and close in a jerky manner, or tics, or other eye movements, such as encountered by people with Tourette's syndrome. As described previously, embodiments of the present invention can be used to monitor g-LOC (loss of consciousness) of pilots caused by positive or negative g-force effects, hypoxemia of passengers or crew in aircraft due to losses in cabin pressure. Embodiments can be used to safely assist anyone who may operate any powered equipment or vehicle and when experiencing any abnormal or adverse change in their biochemical status, or vital signs, such as a cardiac arrhythmia, or asystolic event, or with hypoglycemia. Embodiments can be used to prevent an adverse event, when the operator of equipment has consumed drugs or excessive alcohol, or is operating the equipment or vehicle when drowsy or inattentive. Embodiments disclosed can have application in any environment in which a human operates powered equipment, whereby failure to do so properly can cause harm to the operator or others. If the human physiologic performance decays in the operator of the equipment, because of a physiologic or biochemical change compared to the normal healthy status, the abnormal measured changes can be used to enhance human performance by means of alarms and changes to vehicular or powered equipment in order to prevent an adverse event, record physiological parameters for later analysis, and/or provide a local or remote alarm signal.

Embodiments of the present invention that include the user worn SD/MS display symbology performance enhancement system have application in many fields outside the highly motion provocative military applications, such as non-military motion provocative environments, medical rehabilitation and consumer use. The modular and miniature design of the eye glass subsystem allows the use in a much larger field of use, including vehicular travel (land, sea and air), medical rehabilitation, space travel, microgravity, and space and/or microgravity return rehabilitation, consumer use and integration with operator control interfaces.

Vehicular Travel. The most obvious use for a technology to prevent SD/MS is in an environment where movement alters our normal sense of perception and visual cues such as moving in a variety of vehicles.

High Performance Fighters—Legacy Systems. There are uses for this technology in the systems that still use helmets but do not use HMD technology—the number of legacy systems far exceeds the HMD used and will continue for a number of years. By integrating our technology into pilot eyewear and HMDs, we can improve mission-effectiveness and human performance, while decreasing the probability for loss of aircraft and life. Additionally, our technology will help solve MS in military pilot training Motion sickness significantly impacts the student's physical performance by reducing cognitive and motor abilities. Students routinely leave pilot training due to their continual battle with MS. Using the present systems to effectively combat MS in flight students will: 1) improve pilot performance, enabling them to focus on and master tasks more quickly; 2) reduce student pilot attrition rates due to "active" MS (vomiting); and 3) increased student pilot confidence which leads to better pilot training and increased retention. The SD/MS avoidance system can obtain similar results for crew use within tactical and strategic Air Force operations.

High Performance Fighters—Helmet Mounted Display (HMD) Systems Users. The modular nature of our new software and firmware allows the integration of this technology into the already existing sensor and display suites associated with 4th and 5th generation fighter aircraft HMDs including JHMCS (Joint Helmet Mounted Cueing Systems) By integrating our technology into HMDs and JHMCSs, we can improve mission-effectiveness and human performance, while decreasing the probability for loss of aircraft and life. The near focused feature of our symbology, coloration and shape allow the technology to be effective while de-conflicting with aircraft control and targeting displays.

Tanker, Airlift, Support. We envision tanker, airlift and support aircraft as well a crew members who operate in the back of these vehicles will employ the eyeglass device to improve mission-effectiveness and human performance, while decreasing the probability for loss of aircraft and life.

Helicopter. Rotary wing aircraft are particularly capable of generating high motion provocative environments due to extreme vibration, the visual flash of the rotor blades in various lighting conditions and unique maneuvering capabilities.

Flash Vertigo. There are many case examples where helicopter operators/passengers have encountered extremely adverse physical effects due to the flickering or flashing of light through the rotating blades of the helicopter. Some of the most severe have resulted in epileptic fit, stroke and of course vertigo and MS. Use of the new technology is expected to greatly reduce the negative effects associated with the strobe effects of rotor wing vehicles.

Brown-out. Rotary wing operators often experience loss of visual cues and a sensation of downward velocity increase and/or disorientation when landing in blowing or loose sand environments. It is believed our technology will help alleviate the disorientation associated with the "brown out" phenomenon.

Naval, Shipboard Simulator Training Naval aircrew members assigned aboard ships who engage in flight simulator training on those ships often are affected by motion sickness. This occurs because the motion of the ship and associated vestibular stimulus creates a mismatch with visual cues viewed in the simulator. Additionally the simulator results in a loss of visual cues regarding the shipboard environment. It is believed our technology will prevent motion sickness that occurs during ship board flight simulator training Naval, Aggravated Sea States. Sailors stationed aboard naval ships and merchant marine vessels have long been susceptible to motion sickness associated with the vessel movements that occur during aggravated sea states. It is estimated that nearly every person ever stationed aboard a marine vessel for a prolonged status has suffered mild to debilitating sea sickness. It is believed our technology will prevent/alleviate the symptoms of sea sickness aboard ships.

Counter Vertigo in Virtual Pilot Vehicle Interface. Operators of unmanned aerial systems routinely experience spatial disorientation due to limited visual cues in sensor control displays. Further, experiments using a virtual pilot vehicle control interface, where the pilot controlled the UAS based on visual cues derived directly through sensors (placing the point of view on the nose of the aircraft) versus via CRT control displays led to cases of SD and motion sickness. It is believed our technology will prevent SD/MS in both UAS PVI environments.

Civil and Military Flight Operations. SD/MS causes degradation of human performance (affecting cognitive and motor skills), with resultant loss of expensive equipment and human life. The Aviation Safety Foundation of the Aircraft Owners and Pilots Association indicates an aircraft accident or mishap attributed to SD occurs approximately every 11 days. These accidents have resulted in a fatality rate of 91% in the General Aviation (GA) community and a 69% fatality rate in the U.S. Military. From 1980-2000, the USAF experienced 1,087 aviation fatalities with over 14% (172) directly attributed to SD at a cost of over $1.54B.

Operators. There are over 650,000 civilian pilots in the United States alone. According to the FAA there is an estimated SD related mishap every 11 days in the US. Non-instrument rated pilots who fly into the clouds historically have 178 seconds before ground impact. It is believed our technology can provide the visual cues necessary to combat SD in the civil aircraft flight environment.

Passengers. Passengers in commercial air carriers, business and general aviation aircraft routinely experience motion sickness from vestibular upset and loss of visual cues. It is believed our technology can prevent the SD and MS for passengers aboard all type of civil aircraft.

Space Flight Operations—Micro-gravity. NASA reports that nearly every astronaut is stricken with "space sickness" associated with the loss of balance due to micro-gravity environments. The only remedy at this moment is drug therapy while stationed in space, a decidedly non-optimal solution. Additionally during training for space flight students aboard the zero-G flight simulator routinely experience motion sickness. It is expected our technology will remedy space sickness and by providing visual cues to offset the loss of proprioception and orientation due to loss of gravitation, with the use of orientation sensing elements.

Space Re-entry Rehabilitation. Astronauts returning from extend space flights routinely have to learn to reorient themselves in the terrestrial environment. Motor and cognitive skills are often observed to be severely degraded during the re-acclimation period. This is due to the sudden reintroduction of gravitational cues and stimulus of proprioceptors. The time needed to re-acclimate to the terrestrial environment is about three days per week in space. It is expected our technology will greatly reduce the time to re-acclimate to the terrestrial environment by providing strong visual cues to help orientation in conjunction with the increase in cues provided by reintroduction of gravitation.

Medical Rehabilitation. Presently, 10 million patients receive balance (vertigo) therapy costing $1 billion annually. Reasons for treatment are due to disease affecting the vestibular organs, rehabilitation from surgery on the balance organs, recovery from trauma to the head and rehabilitation in patients learning to use prosthetics in the lower extremities. Clinical tests conducted by the inventor funded by the National Institutes of Health (NIH) resulted in 96% effectiveness in resolving balance issues associated with these various maladies.

Overcome Chronic Illness. Many patients with the NIH test group with chronic balance disorders were able to return to functionality after enduring years of other ineffective treatments. The visual display reduced the average number of clinical visits from 25 rehabilitation treatments to 5 and in several cases proved to be the only effective treatment the patient had ever experienced.

Recovery from Surgery. Within the NIGH test group, the visual display proved to reduce the average number of clinical visits from Twenty-Five (25) rehabilitation treatments to Five (5) and in several cases proved to be the only treatment effective.

Recovery from Trauma. Head trauma and injury to the inner ear often results temporary balance problems. The loss of proprioception with injuries to extremities can also result in loss of balance. In tests the visual display greatly shortened rehabilitation and recovery times and in some cases was the only treatment effective to aid recovery due to head trauma, vestibular injury and limb injury.

Rehabilitation using Prosthetics to Lower Extremities. Physicians associated with the US Army Center for the Intrepid, based at Brook Army Medical Center in San Antonio Tex. report that many soldiers who have suffered injury to the lower extremities or amputation have balance issue while learning to use prosthetics. This is due in part to loss of proprioception inputs associated with the loss of the limbs and new weight distribution associated with the prosthetics. It is hypothesized our technology will greatly shorten rehabilitation time by providing strong visual cues to offset the loss of sense of touch due to limb loss and aid balance while learning to use the new limbs.

Consumer Use. Our technology is deemed to be agnostic in that it can be integrated into a number of carriers and used to prevent SD/MS in nearly any environment where there is a loss of visual cues and or proactive motion. The latest design allows the application of our technology in a myriad of non-clinical, consumer focused activities. Numerous individuals are afflicted by SD and MS in a variety of activities, such as riding in automobiles or buses, taking ocean cruises, deep sea or sport fishing, etc.

Augmented Reality. Augmented Reality systems use sensors to analyze the scene being viewed by the user, enhance the see through visual display using information contained in an internal database and special use algorithms and then display enhanced information to fill in information not actually visible to the wearer. This enhancement may be augmented by activating the SD/MS display symbology based on the optical tracker inputs and overlay ground position awareness or g information. In alternative embodiments the augmented reality provided to the user may be views of the aircraft position in space such as external or "God's eye view" or predicted flight path together with the SD/MS display symbology.

Sports Applications. In nearly every sports activity that features the loss of visual cues or motion provocative environment such as sailing, rock climbing, and auto racing participant's remark on the loss of situation awareness, disorientation or occasional motion sickness. It is expected the use of our technology will prevent SD/MS in these environments by providing strong visual cues to counter the effects of sensory mismatch associated with these motion provocative environments.

Offshore Fishing. It is highly common for at least one person in the party of any recreational offshore fishing boat to become seasick. As already alluded above in the naval section, our technology is expected to be highly effective in the prevention and control of MS in person aboard small marine vessels.

Cruise ships. Of over Twelve and a half Million (12.6 million) passengers who cruise annually it is estimated greater than 20% become seasick. Our technology is expected to be highly effective in controlling MS associated with leisure ship board cruises.

Reading during Vehicular Travel. Many people become carsick when sitting in the back of a moving vehicle with reduced visual cues and increased vibration and even more still when attempting to read in this motion provocative environment. Our technology will provide strong visual cues to counteract the loss of peripheral visual cues and offset the effect of vibration in the ground transportation environment.

Theme Parks. It is highly common for tourists visiting theme parks to become disoriented or experience motion sickness riding them park rides. This is due to the nature of the attractions themselves that either generate extreme motion provocative environments or provide visual cues that have the same effect by showing extremely provocative visual displays. Our technology can prevent motion sickness by providing overriding visual cues that show the true orientation of the passenger with respect to the ground. The glasses are expected to be most effective in countering SD/MS in rides that use high fidelity visual displays since the passenger would be able to verify his/her actual position vice the suggested position from the visual display.

Gaming Applications. A number of modern electronic games feature a virtual control interface. These displays are often not see-through and present highly motion provocative visual displays. Our technology overlaid on the virtual gaming interface would counteract the lack of visual cues and show the gamer true position in space, thus lowering SD and improving situational awareness.

PDA Interface. Our technology carrier currently uses an umbilical that could plug into an i-Phone or i-Pod and could be upgraded in future generations using Bluetooth technology. Using either technique we have the capability to interface with Personal Data Assistants (PDAs). It is possible for the battery to be charged using the interface and for PDA information to be displayed on the glasses.

Adaptation to Various Carriers The modular nature of our sub components and software suite allow for the integration the SD/MS system into other head worn devices other than glasses, or HMD such as night vision equipment, binoculars, goggles, SCUBA masks and any other user worn device. The system can also be integrated with non-head worn display devices such as HUD which display information on a view screen.

While the disclosure has been described with respect to a limited number of embodiments, those skilled in the art, having benefit of this disclosure, will appreciate that other embodiments may be devised which do not depart from the scope of the disclosure as disclosed herein. The disclosure has been described in detail, it should be understood that various changes, substitutions and alterations can be made hereto without departing from the spirit and scope of the disclosure.

What is claimed is:

1. A system comprising:
   a unit attachable to a person's head wherein the head-attachable unit further comprises:
   an orientation sensing element responsive to rotation about a first axis representing a rotation selected from the group consisting of:
   pitch of the person's head and
   roll of the person's head; and
   an eye sensor comprising a video camera, wherein the video camera is responsive to
   palpebral movement as a result of a physiological effect including one or more of vertigo, motion sickness, motion intolerance, or spatial disorientation;
   a head-attachable display viewable by the person wherein the head-attachable display comprises:
   a display driver;
   a see-through region that provides a view substantially similar to what the person would see without wearing the head-worn unit;
   a first image that is not responsive to pitch of the person's head and not responsive to roll of the person's head;
   at least one display element viewable by the person wherein the display element is responsive to a palpebral movement signal from the video camera and responsive to the orientation sensing element; and
   an electronic interface configured for transmitting palpebral movement information received by the video camera to a device selected from the group consisting of a vehicle or powered equipment.

2. The system of claim 1 wherein:
   the orientation sensing element is responsive to pitch of the person's head and roll of the person's head wherein:
   pitch represents a rotation about a first axis representing up and down movement of the person's face while the rear of the person's head moves in the opposite direction and roll represents rotation about a second axis perpendicular to the pitch axis in which the face rotates about the nose when looked at from the front;
   the orientation sensing element comprises:
   a circuit board;

interface circuitry;
communications circuitry;
logic circuitry;
a central processing unit;
a memory unit;
sensor data pre-processing circuitry; and
a micro-electro-mechanical system integrated circuit wherein the micro-electro-mechanical system further comprises an accelerometer;

the eye sensor further measures palpebral position;
the palpebral movement measured by the eye sensor comprises palpebral closure rate, palpebral closure duration, palpebral fissure height, palpebral aperture, marginal reflex distance, frequency of palpebral closure, and velocity of palpebral closure;
system further comprises biosensors the measure electroencephalographic changes, blood pressure, pulse, oxygen saturation, blood glucose, and alcohol level;
the system further comprises an algorithm for determining whether measured palpebral movement is a normal or an abnormal response resulting from a physiological effect including one or more of vertigo, motion sickness, motion intolerance, or spatial disorientation;
the algorithm is responsive to ptosis;
the display further comprises a second image responsive to a pitch signal and a roll signal from the orientation sensing element;
the electronic interface transmits a signal indicating that palpebral movement is abnormal in response to the algorithm; and
the system further comprises an auditory alarm responsive to the algorithm.

3. A system comprising a unit attachable to a person's head wherein the head-attachable unit further comprises:
an orientation sensing element responsive to rotation about a first axis representing a rotation selected from the group consisting of:
pitch of the person's head and
roll of the person's head; and
an eye sensor comprising a video camera, wherein the video camera is responsive to eye closure;
a display viewable by the person wherein the display comprises:
a first image that is not responsive to pitch of the person's head and not responsive to roll of the person's head;
a second image responsive to the orientation sensing element; and
at least one display element viewable by the person wherein the display element is responsive to a palpebral movement signal from the video camera;
an electronic interface configured for transmitting eye sensor information received by the video camera to a device selected from the group consisting of a vehicle or powered equipment.

4. The system of claim 3 wherein:
the orientation sensing element comprises:
a circuit board;
interface circuitry;
communications circuitry;
logic circuitry;
a central processing unit;
a memory unit;
sensor data pre-processing circuitry; and
an orientation sensing element selected from the group consisting of an accelerometer and a gyroscope;

the eye closure measured by the eye sensor comprises eye closure rate, eye closure duration, frequency of eye closure, and velocity of eye closure;
the system further comprises an algorithm for determining whether measured eye closure is a normal or an abnormal response resulting from a physiological effect including one or more of vertigo, motion sickness, motion intolerance, or spatial disorientation; and
the electronic interface transmits a signal indicating that eye closure is abnormal in response to the algorithm.

5. The system of claim 3 wherein:
the eye closure measured by the eye sensor comprises eye closure rate, eye closure duration, frequency of eye closure, and velocity of eye closure;
the system further comprises an algorithm for determining whether measured eye closure is a normal or an abnormal response resulting from a physiological effect including one or more of vertigo, motion sickness, motion intolerance, or spatial disorientation;
the electronic interface transmits a signal indicating that eye closure is abnormal in response to the algorithm.

6. The system of claim 3 wherein:
the orientation sensing element is responsive to pitch of the person's head and roll of the person's head wherein:
pitch represents a rotation about a first axis representing up and down movement of the person's face while the rear of the person's head moves in the opposite direction and roll represents rotation about a second axis perpendicular to the pitch axis in which the face rotates about the nose when looked at from the front;
the orientation sensing element comprises:
a circuit board;
interface circuitry;
communications circuitry;
logic circuitry;
a central processing unit;
a memory unit;
sensor data pre-processing circuitry; and
a micro-electro-mechanical system integrated circuit wherein the micro-electro-mechanical system further comprises an accelerometer.

7. The system of claim 3 wherein:
the eye sensor further measures palpebral position; and
the eye closure information measured by the eye sensor comprises eye closure rate, eye closure duration, eyelid fissure height, eyelid aperture, marginal reflex distance, frequency of eye closure, and velocity of eye closure as a result of a physiological effect including one or more of vertigo, motion sickness, motion intolerance, or spatial disorientation.

8. The system of claim 3 wherein the video camera is further responsive to temporal involuntary eyelid movement as a result of a physiological effect including one or more of vertigo, motion sickness, motion intolerance, or spatial disorientation.

9. The system of claim 3 wherein the display is a head-worn display.

10. The system of claim 3 wherein the eye closure information measured by the eye sensor comprises a condition selected from the group consisting of eye closure rate, eye closure duration, eyelid fissure height, eyelid aperture, marginal reflex distance, frequency of eye closure, and velocity of eye closure.

11. The system of claim 3 wherein:
the system further comprises a vehicle selected from the group of a road vehicle, a flying vehicle, and a vehicle for water-based travel; and the electronic interface transmits the eye sensor information to the vehicle.

12. The system of claim 3 wherein the eye sensor is further responsive to eye movement.

13. The system of claim 3 wherein the eye sensor is further responsive to corneal reflections.

14. The system of claim 3 wherein:
the eye sensor is for sensing eye closure in both the left eye and the right eye.

15. The system of claim 3 wherein the display further comprises:
a first horizon line in a location fixed on the display; and
a second horizon line responsive to an orientation sensor.

16. An eyelid position detection method, the method comprising the steps of:
establishing a portable head-attachable unit wherein establishing further comprises a video-camera-based eye sensor and a head-worn see-through display;
attaching the head-attachable unit to a user's head in a location that allows the user to see the display and allows the eye sensor to see at least one of the person's eyes;
measuring a first eyelid position at a first time wherein measuring further comprises using the eye sensor to detect user eyelid position;
measuring a second eyelid position at a second time;
generating a signal in response to the first eyelid position signal and the second eyelid position signal;
presenting an image on the display wherein the image is responsive to the signal;
establishing an orientation sensing element on the portable head-attachable unit; and
presenting a user viewable display element on the display wherein the display element is responsive to the orientation sensing element.

17. The method of claim 16 wherein:
the orientation sensing element is responsive to pitch and roll of the portable head-attachable unit;
generating a signal further comprises generating a signal in response to the first eyelid position and the second eyelid position selected from the group consisting of eyelid closure rate; eyelid closure duration, eyelid fissure height, eyelid aperture, marginal reflex distance, eyelid closure frequency, and velocity of eyelid closure;
the method further comprises the step of transmitting the signal to a device selected from the group consisting of a vehicle or powered equipment; and
the method is used to monitor a physiological effect including one or more of vertigo, motion sickness, motion intolerance, or spatial disorientation.

18. The method of claim 16 wherein the method is used to monitor a physiological effect including one or more of vertigo, motion sickness, motion intolerance, or spatial disorientation.

19. The method of claim 16 wherein:
generating a signal further comprises generating an alarm signal in response to the first eyelid position and the second eyelid position wherein the alarm signal is in response to eyelid position information selected from the group consisting of eyelid closure rate; eyelid closure duration, eyelid fissure height, eyelid aperture, marginal reflex distance, eyelid closure frequency, and velocity of eyelid closure; and
the method further comprises the step of transmitting the alarm signal to a device selected from the group consisting of a vehicle or powered equipment.

20. The method of claim 16 wherein:
measuring further comprises measuring at least 100 eyelid positions and;
the method further comprises the step of storing the measured eyelid positions in a computer-readable memory for later retrieval.

* * * * *